United States Patent
Groothuis et al.

(10) Patent No.: US 9,724,084 B2
(45) Date of Patent: Aug. 8, 2017

(54) DEVICES AND METHODS FOR PERCUTANEOUS TRICUSPID VALVE REPAIR

(71) Applicant: Mitralign, Inc., Tewksbury, MA (US)

(72) Inventors: Adam Groothuis, Swampscott, MA (US); Steven Cahalane, Pelham, NH (US); Richard Morrill, North Billerica, MA (US); John Alexander, Pinehurst, NC (US)

(73) Assignee: MITRALIGN, INC., Tewksbury, MA (US)

( * ) Notice: Subject to any disclaimer, the term of this patent is extended or adjusted under 35 U.S.C. 154(b) by 444 days.

(21) Appl. No.: 14/190,732

(22) Filed: Feb. 26, 2014

(65) Prior Publication Data

US 2014/0243894 A1 Aug. 28, 2014

Related U.S. Application Data

(60) Provisional application No. 61/769,738, filed on Feb. 26, 2013.

(51) Int. Cl.
*A61B 17/04* (2006.01)
*A61B 17/00* (2006.01)

(52) U.S. Cl.
CPC ..... *A61B 17/0401* (2013.01); *A61B 2017/00783* (2013.01); *A61B 2017/0406* (2013.01);
(Continued)

(58) Field of Classification Search
CPC ......... A61B 17/0401; A61B 2017/0406; A61F 2/2463; A61F 2/2442
See application file for complete search history.

(56) References Cited

U.S. PATENT DOCUMENTS

| | | |
|---|---|---|
| 5,332,402 A | 7/1994 | Teitelbaum |
| 5,733,331 A | 3/1998 | Peredo |

(Continued)

FOREIGN PATENT DOCUMENTS

| | | |
|---|---|---|
| CN | 102869318 | 1/2013 |
| WO | WO 2008/112740 | 9/2008 |

(Continued)

OTHER PUBLICATIONS

International Search Report and Written Opinion in corresponding International Application No. PCT/US14/18720, mailed May 19, 2014.

*Primary Examiner* — Thomas McEvoy
(74) *Attorney, Agent, or Firm* — Leason Ellis LLP

(57) ABSTRACT

The present teachings provide devices and methods of treating a tricuspid valve regurgitation. Specifically, one aspect of the present teachings provides devices and methods of identifying a suitable location on the tricuspid annulus, another aspect of the present teachings provides devices and methods of placing a wire across the tricuspid annulus at such an identified location, another aspect of the present teachings provides devices and methods of deploying a tissue anchor across such an identified location, and yet another aspect of the present teachings provides devices and methods of applying tension to two or more of such tissue anchors and reducing the circumference of the tricuspid annulus. As a result, a regurgitation jet is reduced or eliminated.

13 Claims, 20 Drawing Sheets

(52) U.S. Cl.
CPC ........... *A61B 2017/0409* (2013.01); *A61B 2017/0419* (2013.01); *A61B 2017/0464* (2013.01)

(56) References Cited

U.S. PATENT DOCUMENTS

| | | | |
|---|---|---|---|
| 5,810,746 | A | 9/1998 | Goldstein et al. |
| 6,074,417 | A | 6/2000 | Peredo |
| 6,629,534 | B1 | 10/2003 | St. Goar |
| 7,431,726 | B2 | 10/2008 | Spence et al. |
| 8,029,556 | B2 | 10/2011 | Rowe |
| 8,475,525 | B2 | 7/2013 | Maisano et al. |
| 8,845,717 | B2 | 9/2014 | Khairkhahan et al. |
| 8,888,843 | B2 | 11/2014 | Khairkhahan et al. |
| 8,961,594 | B2 | 2/2015 | Maisano et al. |
| 8,961,596 | B2 | 2/2015 | Maisano et al. |
| 2002/0107531 | A1 | 8/2002 | Schreck et al. |
| 2003/0120340 | A1 | 6/2003 | Liska et al. |
| 2003/0199974 | A1* | 10/2003 | Lee .............. A61F 2/2451 623/2.36 |
| 2004/0162610 | A1 | 8/2004 | Liska et al. |
| 2005/0119734 | A1 | 6/2005 | Spence et al. |
| 2005/0267571 | A1* | 12/2005 | Spence .......... A61B 17/0401 623/2.11 |
| 2006/0229708 | A1 | 10/2006 | Powell et al. |
| 2007/0010857 | A1 | 1/2007 | Sugimoto et al. |
| 2009/0076547 | A1 | 3/2009 | Sugimoto |
| 2009/0093670 | A1 | 4/2009 | Annest et al. |
| 2009/0292353 | A1 | 11/2009 | Yoganathan et al. |
| 2010/0063586 | A1 | 3/2010 | Hasenkam |
| 2010/0070028 | A1 | 3/2010 | Sugimoto |
| 2010/0210899 | A1 | 8/2010 | Schankereli |
| 2010/0292785 | A1 | 11/2010 | Seguin et al. |
| 2011/0015476 | A1 | 1/2011 | Franco |
| 2011/0060407 | A1 | 3/2011 | Ketai |
| 2011/0071626 | A1 | 3/2011 | Wright |
| 2011/0184510 | A1 | 7/2011 | Maisano et al. |
| 2012/0029627 | A1 | 2/2012 | Salahieh et al. |
| 2012/0035712 | A1 | 2/2012 | Maisano et al. |
| 2012/0203336 | A1 | 8/2012 | Annest |
| 2012/0310840 | A1 | 12/2012 | Colombo et al. |
| 2013/0018459 | A1 | 1/2013 | Maisano et al. |
| 2013/0046380 | A1 | 2/2013 | Maisano et al. |
| 2014/0114390 | A1 | 4/2014 | Tobis et al. |
| 2014/0243859 | A1 | 8/2014 | Robinson |
| 2014/0243894 | A1 | 8/2014 | Groothuis et al. |
| 2014/0350662 | A1 | 11/2014 | Vaturi |
| 2015/0025553 | A1 | 1/2015 | Del Nido et al. |
| 2015/0112429 | A1 | 4/2015 | Khairkhahan et al. |
| 2015/0119936 | A1 | 4/2015 | Gilmore et al. |
| 2015/0119979 | A1 | 4/2015 | Maisano et al. |
| 2015/0164637 | A1 | 6/2015 | Khairkhahan et al. |

FOREIGN PATENT DOCUMENTS

| | | |
|---|---|---|
| WO | WO 2012/004679 | 1/2012 |
| WO | WO 2012/178115 | 12/2012 |
| WO | WO 2014/134183 | 9/2014 |

* cited by examiner

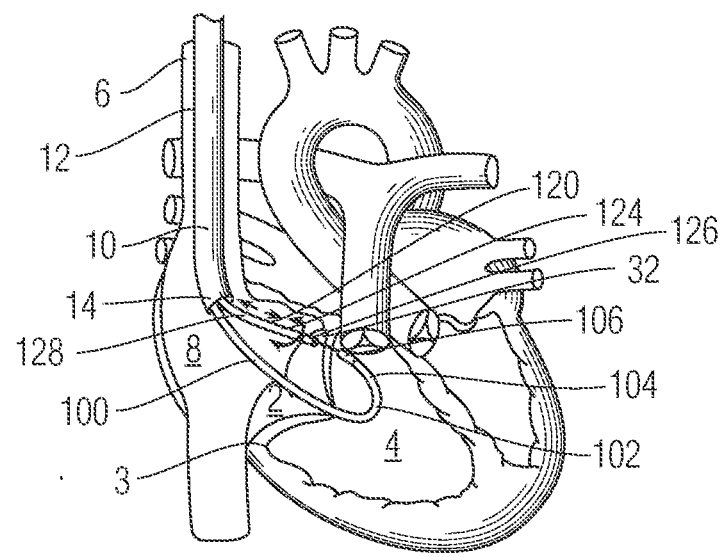
Fig. 7b
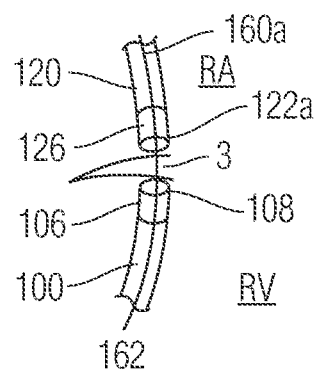 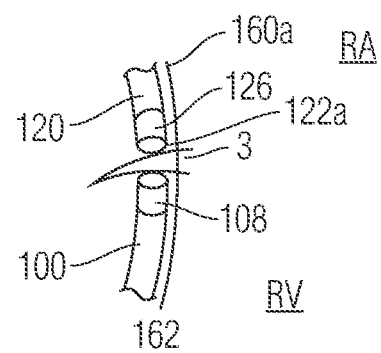
Fig. 7c　　　　Fig. 7d

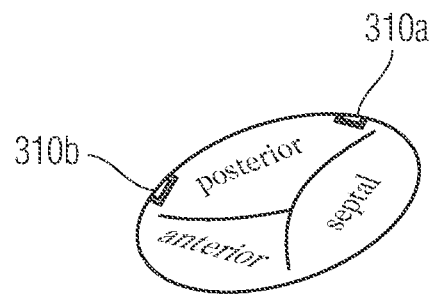 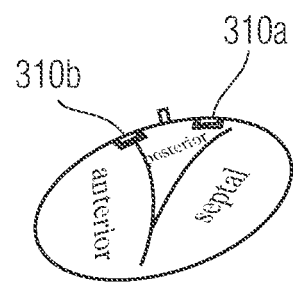
Fig. 16a  Fig. 16b
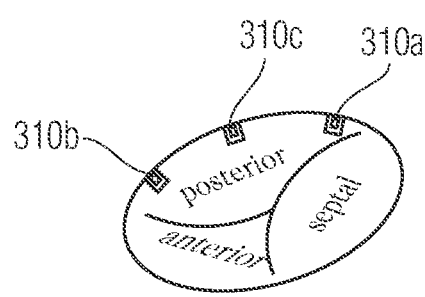 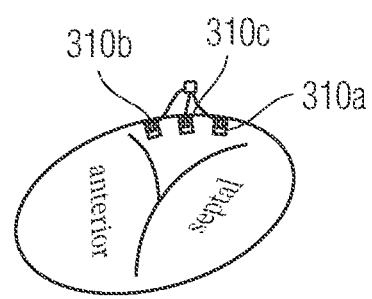
Fig. 16c  Fig. 16d

DEVICES AND METHODS FOR PERCUTANEOUS TRICUSPID VALVE REPAIR

CROSS REFERENCE TO RELATED APPLICATION

This application claims the benefit of U.S. patent application Ser. No. 61/769,738, filed Feb. 26, 2013, which is hereby incorporated by reference in its entirety.

TECHNICAL FIELD

The present teachings generally relate to percutaneous valve repair. Some embodiments of the present teachings relate to percutaneous tricuspid valve repair.

BACKGROUND

Tricuspid valve diseases relate to conditions in which the valve between the two right heart chambers (i.e., the right ventricle and the right atrium) doesn't function properly and they often occur with other heart valve problems. An example of tricuspid valve diseases is tricuspid valve regurgitation, where the tricuspid valve doesn't close properly and blood flows back into the right atrium. Another example is tricuspid valve stenosis where the tricuspid valve is narrowed, which reduces the amount of blood flowing into the right ventricle. Yet another example is tricuspid atresia, a congenital heart disease, where a solid wall of tissues blocks the blood from flowing between the two right heart chambers. Yet another example is the Ebstein's anomaly where a malformed tricuspid valve situates at a position lower than the normal in the right ventricle, causing blood to flow back into the right atrium. There are other tricuspid valve diseases generally known to a person with ordinary skill in the art and these tricuspid valve diseases are also included in the present teachings.

A tricuspid valve disease can be corrected by an annuloplasty ring. In some instances, this device is preferred for surgically repairing a defect tricuspid valve. An annuloplasty ring is an anatomically-correct three-dimensional (3D) ring and can flexibly conform to the heart valve opening. This ring is implanted into a defect tricuspid valve and reduces the valve opening. Properly implanted, an annuloplasty ring allows the valve to open and close properly.

Tricuspid valve repair surgery can be done in one of two ways: a minimally invasive surgery or an open-heart surgery. A minimally invasive method involves making a small upper or lower chest incision and inserting valve repairing system/device percutaneously. After the valve is repaired, the incision is closed with dissolving sutures. Advantages of a minimally invasive approach include a shorter recovery time, less post-operation pain, and earlier return to work and normal daily activities.

SUMMARY

One aspect of the present teachings provides a method for percutaneously reducing the circumference of a tricuspid annulus. This method includes a number of steps, the sequence of which can be changed and each of which can be omitted or modified without the method falling outside the scope of the present teachings. An exemplary step includes positioning a wire delivery catheter through the tricuspid valve into the right ventricle. Another exemplary step includes contacting a distal end of the wire delivery catheter with the tricuspid annulus inside the right ventricle at a first location. Another exemplary step includes advancing one end of a wire from the right ventricle across the tricuspid annulus to the right atrium at the first location, where the wire tracks through an axial lumen of the wire delivery catheter. Another exemplary step includes capturing the end of the wire with a capture device deployed inside the right atrium. Another exemplary step includes retracting the capture device proximally to bring the end of the wire outside of the body. Another exemplary step includes tracking a first tissue anchor delivery catheter over the wire and extending the first tissue anchor delivery catheter across the tricuspid annulus so that a distal end of the first tissue anchor delivery catheter resides inside the right ventricle. Another exemplary step includes deploying a first tissue anchor with a distal portion of the tissue anchor positioning against the tricuspid annulus from inside the right ventricle and a proximal portion of the tissue anchor positioning against the tricuspid annulus from inside the right atrium. Another exemplary step includes retracting the end of the wire back into the axial lumen of the wire delivery catheter.

Another exemplary step includes positioning the wire delivery catheter with the distal end of the wire delivery catheter contacting the tricuspid annulus inside the right ventricle at a second location. Another exemplary step includes advancing the end of the wire from the right ventricle across the tricuspid annulus to the right atrium. Another exemplary step includes capturing the end of the wire with a capture device deployed inside the right atrium. Another exemplary step includes retracting the capture device proximally and thereby extending the end of the wire outside of the body. Another exemplary step includes tracking a second tissue anchor delivery catheter over the wire. Another exemplary step includes extending the second tissue anchor delivery catheter across the tricuspid annulus at the second location so that a distal end of the second tissue anchor delivery catheter resides inside the right ventricle. Another exemplary step includes deploying a second tissue anchor with a distal portion of the tissue anchor positioning against the tricuspid annulus from inside the right ventricle and a proximal portion of the tissue anchor positioning against the tricuspid annulus from inside the right atrium. Another exemplary step includes reducing the distance between the first and second tissue anchors.

In other embodiments, a method for percutaneously reducing the circumference of a tricuspid annulus includes a number of other steps, the sequence of which can be changed and each of which can be omitted or modified without the method falling outside the scope of the present teachings. An exemplary step includes positioning a locating catheter through the tricuspid valve into the right ventricle. Another exemplary step includes contacting a distal end of the locating catheter with the tricuspid annulus inside the right ventricle at a first location. Another exemplary step includes advancing a wire delivery catheter into the right atrium with a distal end of the wire delivery catheter opposing the distal end of the locating catheter and contacting the tricuspid annulus inside the right atrium at the first location. Another exemplary step includes advancing a distal end of a wire from the right atrium across the tricuspid annulus to the right ventricle at the first location, wherein the wire tracks through an axial lumen of the wire delivery catheter. Another exemplary step includes tracking a first tissue anchor delivery catheter over the wire. Another exemplary step includes crossing the tricuspid annulus with a distal end of the first tissue anchor delivery catheter inside the right ventricle. Another exemplary step includes deploying a first tissue anchor with a distal portion of the tissue anchor positioning against the tricuspid annulus from inside the right ventricle and a proximal portion of the tissue anchor positioning against the tricuspid annulus from inside the right atrium. Another exemplary step includes retracting the distal end of the wire back into the axial lumen of the wire delivery catheter. Another exemplary step includes positioning the locating catheter with the distal end of the locating catheter contacting the tricuspid annulus inside the right ventricle at a second location. Another exemplary step includes positioning the wire delivery catheter into the right atrium with the distal end of the wire delivery catheter opposite to the distal end of the locating catheter and contacting the tricuspid annulus inside the right atrium at the second location. Another exemplary step includes advancing the distal end of the wire from the right atrium across the tricuspid annulus to the right ventricle. Another exemplary step includes tracking a second tissue anchor delivery catheter over the wire and crossing the tricuspid annulus at the second location with a distal end of the second tissue anchor delivery catheter inside the right ventricle. Another exemplary step includes deploying a second tissue anchor with a distal portion of the tissue anchor positioning against the tricuspid annulus from inside the right ventricle and a proximal portion of the tissue anchor positioned against the tricuspid annulus from inside the right atrium. Another exemplary step includes reducing the distance between the first and second tissue anchors.

In other embodiments, a method for percutaneously reducing the circumference of a tricuspid annulus includes a number of steps, the sequence of which can be changed and each of which can be omitted or modified without the method falling outside the scope of the present teachings. An exemplary step includes positioning a wire delivery catheter through the tricuspid valve into the right ventricle, wherein a multi-lumen translation catheter is slidably disposed within a lumen of the wire delivery catheter, a first wire is slidably disposed within a first catheter member of the multi-lumen translation catheter, a second wire is slidably disposed within a second catheter member of the multi-lumen translation catheter. Another exemplary step includes positioning a distal end of the first catheter member at a first location. Another exemplary step includes advancing one end of the first wire from the right ventricle across the tricuspid annulus to the right atrium at the first location. Another exemplary step includes expanding the second catheter member of the multilumen translation catheter. Another exemplary step includes positioning a distal end of the second catheter member against the tricuspid annulus at a second location. Another exemplary step includes advancing one end of the second wire from the right ventricle across the tricuspid annulus to the right atrium at the second location. Another exemplary step includes capturing the ends of the first and second wires with a capture device. Another exemplary step includes retracting the capture device proximally and extending the ends of the first and second wires outside of the body. Another exemplary step includes tracking a first tissue anchor delivery catheter over the first wire and a second tissue anchor delivery catheter over the second wire. Another exemplary step includes crossing the tricuspid annulus with distal ends of the first and second tissue anchor delivery catheters inside the right ventricle. Another exemplary step includes deploying the first and second tissue anchors with distal portions of the first and second tissue anchors positioning against the tricuspid annulus from inside the right ventricle and proximal portions of the first and second tissue anchors positioning against the tricuspid annulus from inside the right atrium. Another exemplary step includes reducing the distance between the first and second tissue anchors.

In other embodiments, a method for percutaneously reducing the circumference of a tricuspid annulus includes a number of steps, the sequence of which can be changed and each of which can be omitted or modified without the method falling outside of the present teachings. An exemplary step includes positioning a locating catheter through the tricuspid valve into the right ventricle, wherein a multi-lumen translation catheter is slidably disposed within a lumen of the locating catheter and the multi-lumen translation catheter has a first catheter member and a second catheter member. Another exemplary step includes positioning a distal end of the first catheter member at a first location. Another exemplary step includes expanding the second catheter member of the multi-lumen translation catheter and positioning a distal end of the second catheter member against the tricuspid annulus at a second location. Another exemplary step includes advancing first and second wire delivery catheters into the right atrium with distal ends of the first and second wire delivery catheters positioned opposite to the distal ends of the first and second catheter member. Another exemplary step includes contacting the tricuspid annulus inside the right atrium at the first and second locations. Another exemplary step includes advancing distal ends of first and second wires from the right atrium across the tricuspid annulus to the right ventricle at the first and second locations. Another exemplary step includes tracking the first and second tissue anchor delivery catheters over the first and second wires and crossing the tricuspid annulus with distal ends of the first and second tissue anchor delivery catheters inside the right ventricle. Another exemplary step includes deploying the first and second tissue anchors with distal portions of the first and second tissue anchors positioned against the tricuspid annulus from inside the right ventricle and proximal portions of the first and second tissue anchors positioned against the tricuspid annulus from inside the right atrium. Another exemplary step includes reducing the distance between the first and second tissue anchors.

BRIEF DESCRIPTION OF THE DRAWINGS

FIGS. 7a-7b are perspective views of an exemplary locating catheter inserted into the right ventricle in accordance with the present teachings;

FIGS. 7c-7d are perspective views of an exemplary wire across the annulus in accordance with the present teachings;

FIGS. 16a-16f are perspective views of an example of applying tension to multiple exemplary tissue anchors deployed across the tricuspid annulus in accordance with the present teachings;

DETAILED DESCRIPTION OF CERTAIN EMBODIMENTS

Figure 1:
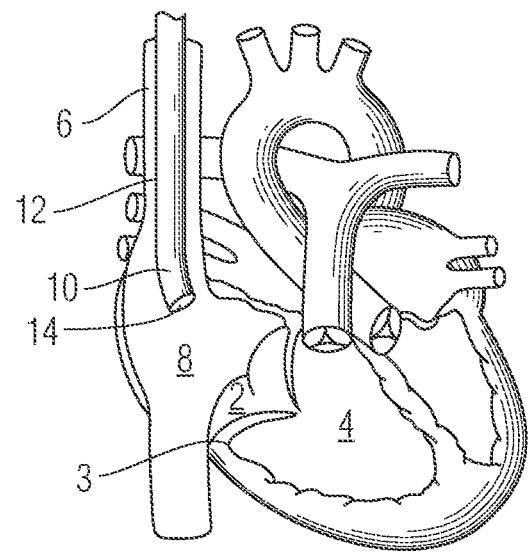
FIG. 1 is a perspective view of an exemplary guide percutaneously inserted into the right atrium in accordance with the present teachings.

Certain specific details are set forth in the following description and figures to provide an understanding of various embodiments of the present teachings. Those of ordinary skill in the relevant art would understand that they can practice other embodiments of the present teachings without one or more of the details described herein. Thus, it is not the intention of the Applicant(s) to restrict or in any way limit the scope of the appended claims to such details. While various processes are described with reference to steps and sequences in the following disclosure, the steps and sequences of steps should not be taken as required to practice all embodiments of the present teachings.

As used herein, the term "lumen" means a canal, a duct, or a generally tubular space or cavity in the body of a subject, including a catheter, a hollow needle, a tube, a vein, an artery, a blood vessel, a capillary, an intestine, and the like.

As used herein, the term "proximal" shall mean close to the operator (less into the body) and "distal" shall mean away from the operator (further into the body). In positioning a medical device inside a patient, "distal" refers to the direction away from a catheter insertion location and "proximal" refers to the direction close to the insertion location.

As used herein, the term "wire" can be a strand, a cord, a fiber, a yarn, a filament, a cable, a thread, or the like, and these terms may be used interchangeably.

As used herein, the term "sheath" may also be described as a "catheter" and, thus, these terms can be used interchangeably.

The following description refers to FIGS. 1 to 19. A person with ordinary skill in the art would recognize that the figures and description thereto refer to various embodiments of the present teachings and, unless indicated otherwise by their contexts, do not limit the scope of the attached claims to the figures and/or description thereto.

Unless otherwise specified, all numbers expressing quantities, measurements, and other properties or parameters used in the specification and claims are to be understood as being modified in all instances by the term "about." Accordingly, unless otherwise indicated, it should be understood that the numerical parameters set forth in the following specification and attached claims are approximations. At the very least and not as an attempt to limit the application of the doctrine of equivalents to the scope of the attached claims, numerical parameters should be read in light of the number of reported significant digits and the application of ordinary rounding techniques.

The present teachings relate to devices and methods for treating a tricuspid regurgitation. An aspect of the present teachings provides various embodiments of locating a first location on the tricuspid annulus (3) (as shown in FIGS. 1 to 19). According to some embodiments, the first location is on the posterior annulus approximate to the commissure of the posterior and septal leaflets or to the commissure of the posterior and anterior leaflets.

A further aspect of the present teachings provides various embodiments of placing a wire across the tricuspid annulus (3) at the first location. According to some embodiments, the wire crosses the tricuspid annulus (3) from the right atrium to the right ventricle (4) (as shown in FIGS. 1 to 19). According to some embodiments, a wire of the present teachings crosses the tricuspid annulus (3) from the right ventricle to the right atrium (8) (as shown in FIGS. 1 to 19).

A further aspect of the present teachings provides various embodiments of deploying a tissue anchor (310a) (as shown, for example, in FIG. 11a) over the wire and across the tricuspid annulus. According to some embodiments, the distal portion of the tissue anchor (310a) is deployed inside the right ventricle (4) and the proximal portion of the tissue anchor (310a) is deployed inside the right atrium (8). According to some embodiments, the distal portion of the tissue anchor (310a) is deployed inside the right atrium (8) and the proximal portion of the tissue anchor (310a) is deployed inside the right ventricle (4).

A further aspect of the present teachings provides various embodiments of locating a second location (30) (as shown, for example, in FIG. 13a) on the tricuspid annulus (3), placing a second wire across the tricuspid annulus (3), and then deploying a second tissue anchor (310) (as shown, for example, in FIG. 14a) across the tricuspid annulus.

A further aspect of the present teachings provides various embodiments of reducing the circumference of the tricuspid annulus (3). An exemplary method of the present teachings begins by percutaneously accessing the tricuspid annulus (3) from a suitable venous access site. According to some embodiments, the venous access site is located near the jugular vein, superiorly, from the femoral vein, inferiorly, or from other suitable sites. According to some embodiments of the present teachings, as illustrated in FIG. 1, a suitable guide (12) is directed into the internal jugular vein, extends through the right brachiocephalic vein, the superior vena cava (6), and reaches the right atrium (8). The distal end (10) of the guide (12) remains inside the right atrium (8). The proximal end (not shown) of the guide (12) remains outside of the body. According to some embodiments, the guide (12) could have a general straight profile. In another embodiment, the guide (12) could have a curved distal portion. In some embodiments, the distal portion of the guide (12) could have a pre-set fixed curved. In another embodiment, the distal portion of the guide (12) could be deflectable curved section controlled by a clinician from outside of the body. The guide (12) has an axial lumen (14) extending from its proximal end through its entire length to its distal end (10). This axial lumen (14) of the guide (2) serves as a conduit, allowing one or more catheters to be slidably disposed within and providing access to the right heart chambers. According to some embodiments, the guide (12) remains in place as illustrated in FIG. 1 during the entire procedure. According to some embodiments, the guide (12) is removed, for example, during the procedure when other suitable means, such as a wire, maintains such a percutaneous access. According to some embodiments, the guide (12) is a 12 French (F) sheath. According to some embodiments, the guide (12) is a single lumen sheath that can accommodate all subsequent catheters to slide therein. Alternatively, in some embodiments, the guide (12) is a multi-lumen sheath. It will be appreciated by persons of ordinary skill in the art that the size and the exact configuration of the guide (12) is not limited to what is disclosed herein.

In various embodiments, a percutaneous repair of the tricuspid valve (2) starts with identifying and obtaining an access to a first location on the tricuspid annulus (3). FIGS. 2-6 illustrate some embodiments where a wire gains an access to the tricuspid valve (2) from the right ventricle (4) and is advanced across the tricuspid annulus (3) into the right atrium (8). Upon doing so, the distal end of the wire extends from the venous access site through the lumen (14) of the guide (12), reaches the right atrium (8), extends distally through the tricuspid valve (2), reaches the right ventricle (4), advances across the tricuspid valve (2) annulus, and extends proximally out of the body through the lumen (14) of the guide (12). As a result, both ends of the wire are outside of the body.

Figure 2A:
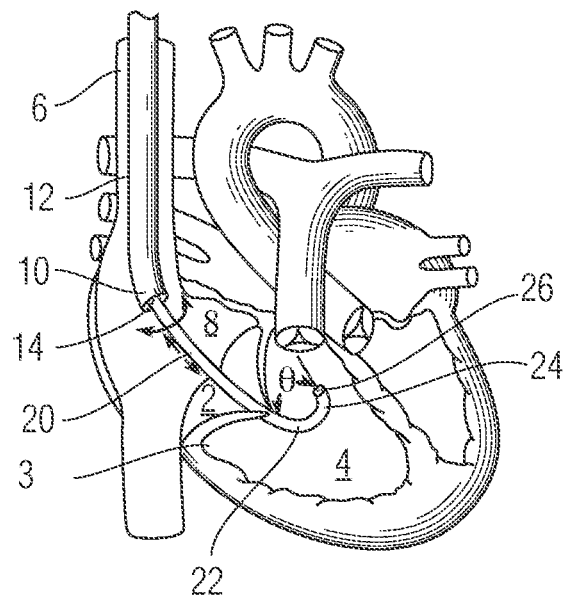
FIGS. 2a-2b are perspective views of an exemplary wire delivery catheter inserted into the right ventricle in accordance with the present teachings.

FIG. 2a illustrates an embodiment where a wire delivery catheter (20) is directed into the right ventricle (4). In one embodiment, a wire delivery catheter is inserted (20) from the proximal end of the guide (12) through the lumen (14) of the guide (12) and reaches the right atrium (8). As shown in FIG. 2a, as the distal end (24) of the wire delivery catheter (20) extends beyond the distal end (10) of the guide (12), the wire delivery catheter (20) is extended further distally through the tricuspid valve (2) and reaches the right ventricle (4). Inside the right ventricle (4), the distal end portion (22) of the wire delivery catheter (20) bends radially away from the longitudinal axis of the wire delivery catheter (20), assuming a curved profile. According to some embodiments, the curved profile of the distal end portion (22) of the wire delivery catheter (20) is in the shape of the letter "J," the letter "U," or any curvature between 90° to 270° as marked as "θ" in FIG. 2a. According to some embodiments, the distal end portion (22) of the wire delivery catheter (20) has a preformed curve, such that as the distal end (24) of the wire delivery catheter leaves the constraint of the guide (12) and enters the right ventricle (4), the distal end portion (22) of the wire delivery catheter (20) resumes its curved profile. According to some other embodiments, the wire delivery catheter (20) has a deflectable distal end portion (22), which is actuated to form a curved profile. One skilled in the art would understand that such an actuation can be accomplished by many mechanisms known in the field. According to some embodiments, the wire delivery catheter (20) can be extended distally, retracted proximally, or turned axially as shown by the double-headed arrows in FIG. 2a.

Figure 2B:
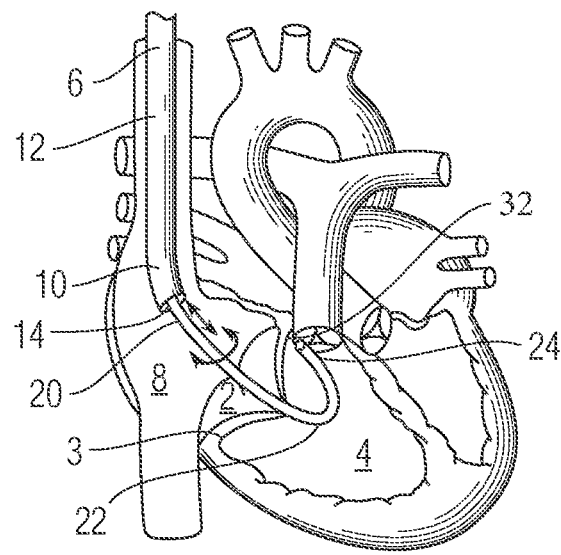

As further illustrated in FIG. 2b, the distal end (24) of the wire delivery catheter (20) is adapted to locate the first location (32) and then make contact with the tricuspid annulus (3) at the right ventricle (4) side.

Anatomically, the right coronary artery is approximately parallel to the circumference of the tricuspid valve (2). The anterior and septal leaflets lie approximately to the proximal half of the right coronary artery. The posterior leaflet of the tricuspid lies approximately to the distal half of the right coronary artery and between the middle of the right coronary artery and the transition of the distal right coronary artery to the posterior descending artery. The middle of the right coronary artery lies approximately next to the commissure of the anterior and posterior leaflets. The transition of the distal right coronary artery to the posterior descending artery, or the proximal posterior descending artery, lies approximately next to the commissure of the septal and posterior leaflets. One skilled in the art would understand that the anatomy of the heart may vary from a subject to another and the present teachings and the attached claims are not limited to the anatomy of any particular subject.

According to some embodiments, a first location (32) is identified by injecting a contrast dye inside the right coronary artery and the distal posterior descending artery. Alternatively, a location can be identified by advancing a radiopaque wire through the right coronary artery to the posterior descending artery. In various embodiments, the contrast dye and/or the radiopaque wire renders the right coronary artery visible under radiographic imaging equipment such as X-ray, magnetic resonance, ultrasound, fluoroscope, or other imaging techniques. By visualizing the right coronary artery and the posterior descending artery, a location can be identified.

Upon identifying the first location (32), in various embodiments, a clinician steers the wire delivery catheter so that, as shown in FIG. 2b, the distal end (24) of the wire delivery catheter (20) aligns at the tricuspid annulus (3), extends toward the right atrium (8), and contacts the tricuspid annulus (3) at the first location (32). According to one embodiment, the first location (32) is at or near the commissure of the septal and posterior leaflets. Alternatively, the first location (32) is at or near the commissure of the anterior and posterior leaflets. One skilled in the art would understand that other locations along the tricuspid annulus (3) can also be used as a first location.

Figure 3A:
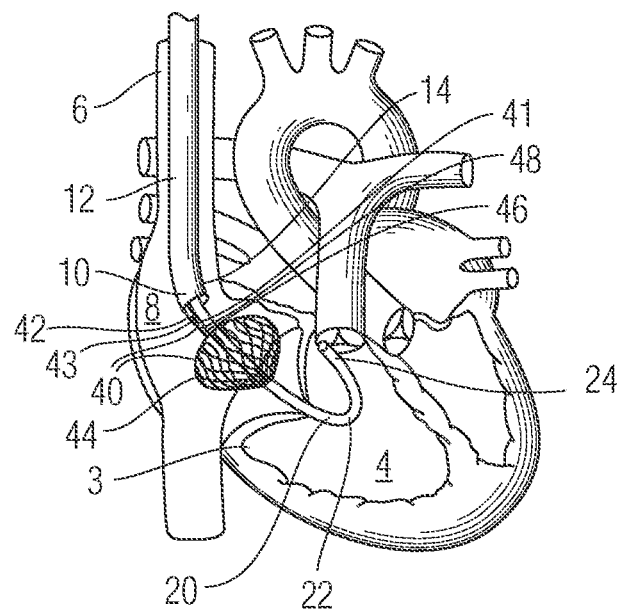
FIGS. 3a-3b are perspective views of an exemplary capture device deployed inside the right atrium in accordance with the present teachings.

In various embodiments, upon aligning the distal end (24) of the wire delivery catheter (20) at the location (32), a capture device (40) is deployed inside the right atrium (8). FIG. 3a illustrates an embodiment where a capture device (40) is advanced distally through the guide (12) and into the right atrium (8). According to some embodiments, a capture device (40) includes a sheath (42) and a capture basket (44). In some embodiments, a capture devices, such as the one illustrated in FIG. 3a, includes a capture basket (44) having an array of shape memory wire mesh on the distal end (48) of a rod (46). According to some embodiments, the capture basket (44) has a radially expanded basket-like profile for capturing the wire as described below and an elongated profile when being constrained within the sheath (42). The capture basket (42) as shown in FIG. 3a is adapted to slide through the axial lumen (41) of the sheath (42), be pushed out of the distal end (43) of the sheath (42), and be retracted back from the distal end (43) of the sheath (42). As the capture basket (44) extends outside of the distal end (43) of the sheath (42), it resumes its expanded profile. As the capture basket (44) is retracted back into the sheath (42), it collapses into its elongated profile. One skilled in the art would understand that the capture basket (44) can be used without the sheath (42), but with the guide (12) alone. Thus what has been described herein should not be viewed as limiting. Additionally, one skilled in the art should understand that although an exemplary embodiment of the capture device has been described in detail herein, other capture device available in the art can also be used for the same purpose to capture the wire. For example a gooseneck snare mechanism can be used. In some embodiment, the snare catheter is constructed of Nitinol cable and with a snare loop. The preformed snare loop can be introduced through catheters without risk of snare deformation because of the snare's super-elastic construction. The snare loop is used to capture the distal end of the wire.

In an exemplary use of the device, as illustrated in FIG. 3a, a capture device (40) having a capture basket (44) constrained to its elongated profile within the sheath (42) is directed through the lumen (14) of the guide (12). According to some embodiments, when a multi-lumen sheath is used as the guide, the capture device (40) extends through a separate lumen from the one used by the wire delivery catheter (20). According to other embodiments, when a single-lumen sheath is used as the guide, the capture device (40) extends side-by-side with the wire delivery catheter (20) through the same lumen of the guide. Once the distal end of the capture device (40) is advanced beyond the distal end (10) of the guide (12) and reaches the right atrium (8), the capture basket (44) is further pushed distally outside of the sheath (42) and, being free from the constraint of the sheath (42), the capture basket (44) deploys. The deployed capture basket (44) can at least partially fill the volume of the right atrium (8). One skilled in the art should understand that multiple guides could also be used, one for the delivery capture device, and the other for the delivery of the wire delivery catheter. Thus the exemplary embodiment disclosure herein should be not viewed as limiting.

Figure 3B:
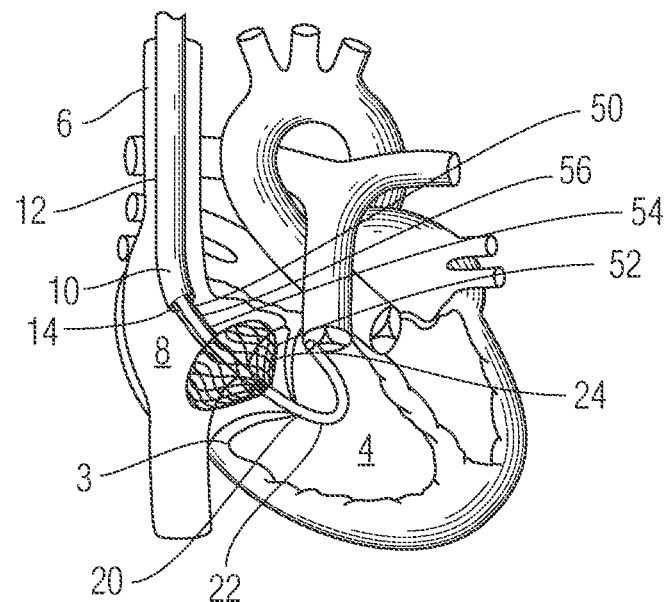

FIG. 3b illustrates another embodiment of the capture device (50). According some embodiments, the capture device (50) includes a capture basket (52) at the distal end (54) of an elongated body (56). The capture device (50), including the elongated body (56) and the capture basket (52) forming an axial lumen, is slidably disposed over the wire delivery catheter (20). Similar to the embodiment shown in FIG. 3a, this capture basket (52) is adapted to slide through the axial lumen (14) of the guide (12). Also similar to the embodiment shown in FIG. 3a, the capture basket (52) has an elongated profile when it is constrained within the lumen (14) of the guide (12) and a radially expanded basket-like profile when it is outside of the guide (12). Similarly, the capture basket (52) can be made of an array of shape memory wire mesh.

According to some embodiments, this capture device (50) is adapted to slide over the wire delivery catheter (20), through the lumen (14) of the guide (12), and be pushed out of the distal end (10) of the guide (12). As the capture device (50) extends outside of the distal end (10) of the guide (12), it resumes its expanded profile. As the capture device (50) is retracted into the lumen (14) of the guide (12), it collapses into its elongated profile. According to some embodiments, the movement of the capture device (50) is independent of the movement of the wire delivery catheter (20). According to other embodiments, the movement of the capture device (50) is dependent to the movement of the wire delivery catheter (20) such that. In certain embodiments, as the distal end (24) of the wire delivery catheter (20) contacts the annulus (3), the capture basket (52) is extended outside of the guide (12) and fully deployed inside the right atrium (8). Although certain embodiments of the capture basket (52) are shown in FIGS. 3a and 3b, one skilled in the art would understand that other capture devices can also be used without departing from the spirit of the present teachings. Thus, what is disclosed in present teachings should not be viewed as limiting.

Besides having a capture basket, according to another embodiment, a capture device includes a sheath with an expandable distal portion or a snare. One skilled in the art would understand that other types of suitable capture devices can also be used here. Thus what is disclosed herein and in FIGS. 3a-3b should not be considered as limiting.

Figure 4A:
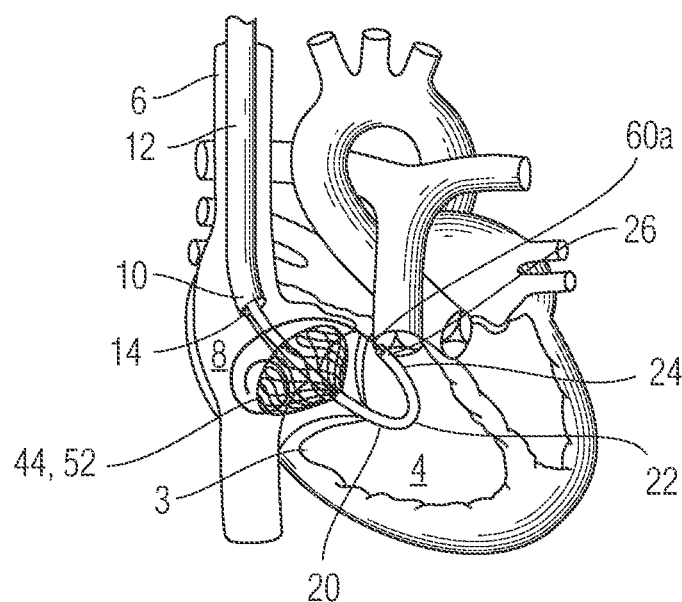
FIGS. 4a-4b are perspective views of an exemplary wire positioned across the annulus in accordance with the present teachings.

In various embodiments, with the capture basket deployed inside the right atrium (8) and the wire delivery catheter (20) properly positioned, a clinician can extend a wire (60a) across the tricuspid annulus (3). Referring to FIG. 4a, a wire is introduced through the wire delivery catheter (20). In the embodiment as illustrated in FIG. 4a, the wire (60a) tracks through the axial lumen (26) of the delivery catheter (20), extends distally from its proximal end, contacts the tricuspid annulus (3), further extends distally, crosses the annulus (3) from the right ventricle (4) side, enters into the right atrium (8), and enters the space filled by the capture basket (44, 52). In some embodiments, the wire is captured by the capture basket.

According to some embodiments, as illustrated in FIG. 4a, the wire (60a) has a piercing tip which allows it to perforate the annulus (3). According to other embodiments, the wire (60a) has a radio frequency (RF) energy delivery tip to assist its crossing of the tricuspid annulus (3). In these other embodiments, a suitable RF energy device (not shown) is coupled to the wire.

Figure 4B:
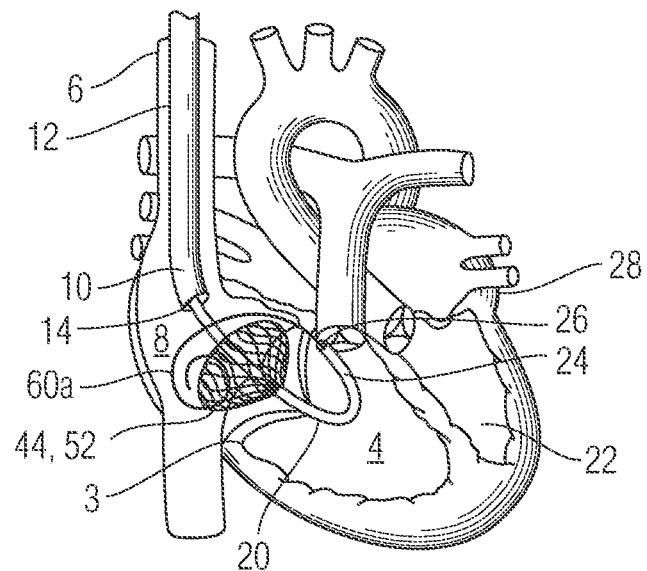

Yet according to other embodiments, as illustrated in FIG. 4b, the wire delivery catheter (20) also includes an extendable needle (28) that is capable of piercing the tricuspid annulus (3). The wire (60a) tracks through the lumen (26) of the such wire delivery catheter (20), extends through the aperture created by the extendable needle (28) of the catheter (20), reaches into the right atrium (8), and enters into the space filled by the capture basket (44, 52). In some embodiments, the wire is captured by the capture basket (44, 52). One skilled in the art would understand that other methods and devices can also be used to access the right atrium (8). Thus, the particular examples described herein should be not viewed as limiting to the scope of the present teachings.

According to some embodiments, the distal portion of the wire (60a) is designed to deflect or curl back to prevent inadvertent tissue damage. The ability to deflect or curl can be achieved by the geometrical construct of the wire (60a), such as a flexible distal portion (62), by the physical property of the material used in making the wire (60a), or by the shape memory property of the material used in making the wire (60a). Those skilled in the art would be able to incorporate known techniques and/or material to achieve this purpose without undue experimentation.

Figure 5:
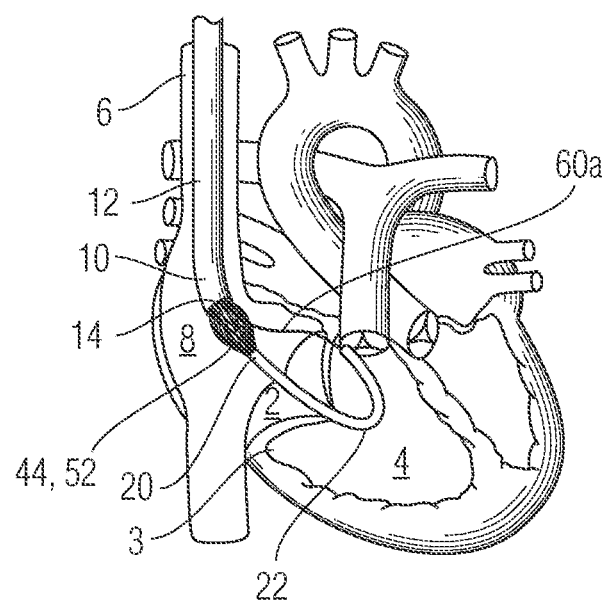
FIG. 5 is a perspective view of an exemplary wire captured and pulled through the guide in accordance with the present teachings.

Now referring to FIG. 5, as the wire enters the right atrium (8) and the space filled by the deployed capture basket (44, 52), it is captured by the capture basket (44, 52) of the capture device (40, 50). As a clinician retracts the capture basket (44) proximally into the sheath (42) or into the guide (12), the capture basket (44, 52) collapses onto the wire (60a). As the clinician further retracts the capture device (40, 50) proximally, the capture device (40, 50) pulls the wire (60a) proximally through the lumen (14) of the guide (12) and out of the body.

Figure 6:
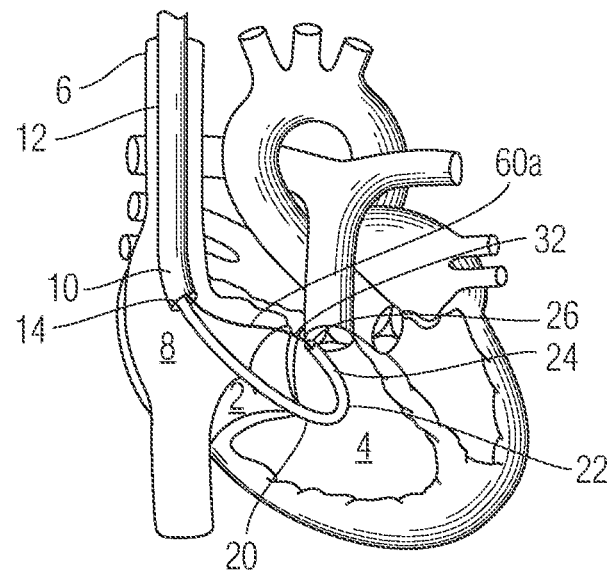
FIG. 6 is a perspective view of an exemplary wire positioned across the annulus in accordance with the present teachings.

In various embodiments, a clinician further retracts the capture device (40), including the sheath (42) and the capture basket (55) as shown in FIG. 3a or including the elongated member (56) with the capture basket (52) as shown in FIG. 3b, proximally through the lumen (14) of the guide (12) outside of the body. By doing this, in some embodiments, the clinician pulls the wire (60a) to the outside of the body. As a result, as shown in FIG. 6, with one end of the wire (60a) remaining outside of the body, the other end extends from the venous access site distally through the lumen (26) of the wire delivery catheter (20), passes the right atrium (8), the tricuspid valve (2), and the right ventricle (4), crosses the tricuspid annulus (3) at a first location (32), extends proximally through the lumen (14) of the guide (12), and exits the venous access site. Thus, with both the ends outside of the body, the wire (60a) maintains an access across the tricuspid annulus (3) at the first location (32) and facilitates the deployment of a tissue anchor (310a) as detailed below.

Figure 8A:
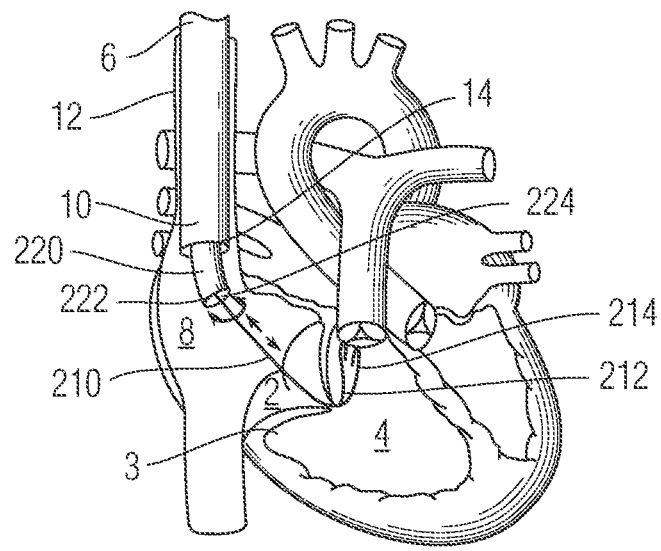
FIGS. 8a-8b are perspective views of an exemplary locating device inserted into the right ventricle in accordance with the present teachings.
Figure 8B:
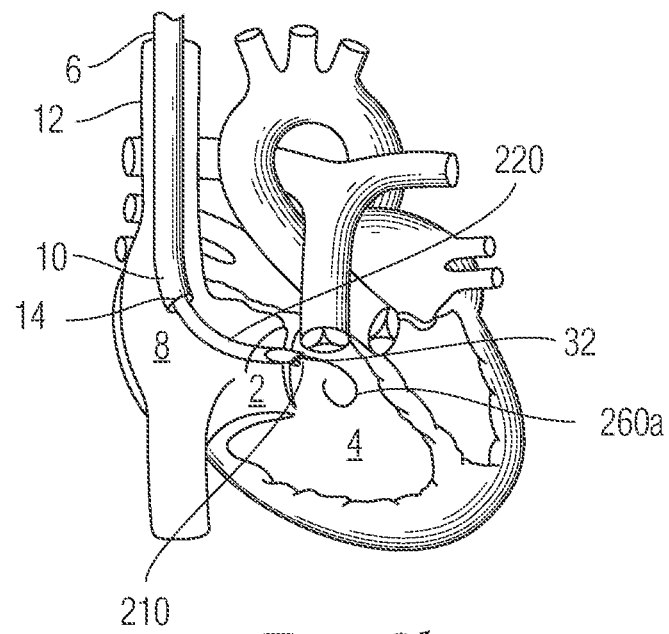
Figure 9:
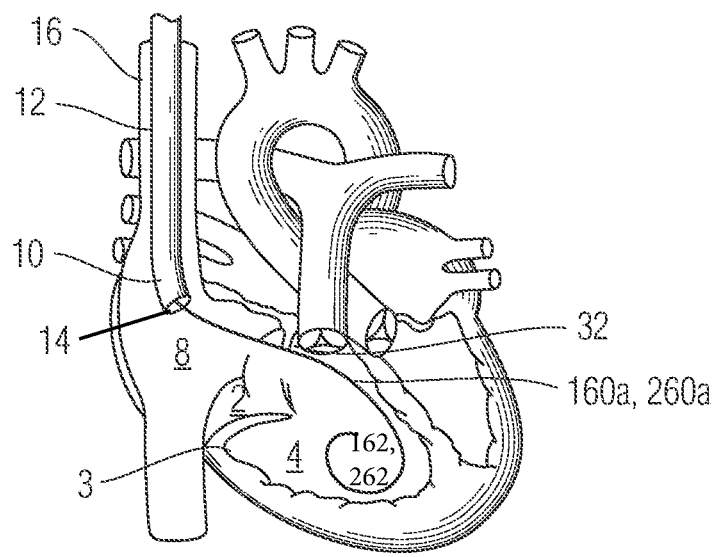
FIG. 9 is a perspective view of an exemplary wire positioned across the annulus in accordance with the present teachings.

FIGS. 7-9 illustrate some embodiments where the wire (160a) extends from the right atrium (8) across the tricuspid annulus (3) into the right ventricle (4) with the proximal end of the wire (160a) outside of the body and the distal end (162) of the wire (160a) inside the right ventricle.

Figure 7A:
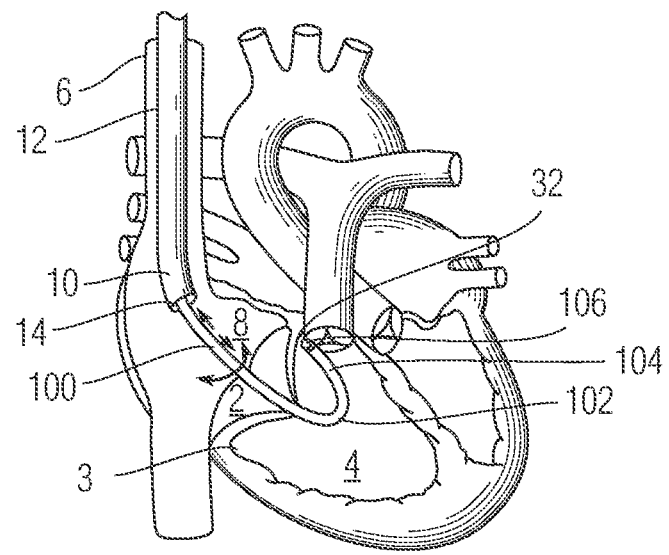

FIGS. 7a-7c illustrate various embodiments where the wire delivery catheter (120) is steered by a locating catheter (100) and positioned against the tricuspid annulus (3) inside the right atrium (8). According to some embodiments, the locating catheter (100) extends distally through the lumen (14) of the guide (12) into the right ventricle (4). In certain embodiments, the locating catheter (100) enters into the right ventricle in a similar manner as the wire delivery catheter (20) described in accordance with FIGS. 2a and 2b. Following the same identification and placement processes as described herein, in various embodiments, the locating catheter (100) is positioned against the tricuspid annulus (3) at the first location (32) inside the right ventricle (4). According to some embodiments, the construct of the locating catheter (100) is similar to the wire delivery catheter (20) described above. In certain embodiments, the locating catheter has a preformed curved distal end portion (102). In certain embodiments, the locating catheter is capable of extending distally and retracting proximally as indicated by the straight double-headed arrows in the FIG. 7a. In certain embodiments, the locating catheter is adapted to turn axially as indicated by the curved double-headed arrows in the FIG. 7a.

Continuing referring to FIG. 7a, in various embodiments, the locating catheter (100) has a magnet (106) at its distal end (104). A wire delivery catheter (120) is advanced distally through the lumen (14) of the guide (12), reaching inside the right atrium (8) and approaching the tricuspid annulus (3). According to some embodiments, the distal end (124) of the wire delivery catheter (120) includes a magnet (126). The magnets (106, 126) on both the locating catheter (100) and the wire delivery catheter (120) have the opposite polarities. Thus, as the wire delivery catheter (120) approaching the tricuspid annulus (3), the magnet in the distal end of the delivery catheter is attracted by the magnet (106) on the distal end (104) of the locating catheter (100). Once the magnets (106, 126) lock up, the tricuspid annulus (3) is sandwiched between the distal ends (124, 102) of the two catheters as illustrated in FIG. 7b.

In various embodiments, a wire (160a) is then advanced from the right atrium (8) across the tricuspid annulus (3) into the right ventricle (4). According to some embodiments, as illustrated in FIG. 7c, the wire (160a) tracks along the axial lumen (122a) of the wire delivery catheter (120) and, upon crossing the tricuspid annulus (3), enters the axial lumen (108) of the locating catheter (100). As the locating catheter (100) retracts proximally, the distal end (162) of the wire (160a) remains inside the right ventricle (4). According to other embodiments, as illustrated in FIG. 7d, the wire (160a) tracks along a side or off-centered axial lumen (122b) of the wire delivery catheter (120) and, upon crossing the tricuspid annulus (3), the distal end (162) of the wire (160a) enters the right ventricle (4). According to some embodiments, the wire delivery catheter (120) also has a deflectable distal end portion (128), which allows this distal end portion (128) deflect radially when the magnet (126) at the distal end (124) of the wire delivery catheter (120) is drawn to the location (32) by the magnet (106) at the distal end (104) of the locating catheter (100), as shown in FIG. 7b. Similarly, the wire delivery catheter (120) can be extended distally and retracted proximally or turned axially, as indicated by the double-headed arrows. According to some embodiments, the design or configuration of the wire (160a) is similar to what is described herein in according with FIGS. 4a and 4b.

FIGS. 8a and 8b illustrate yet other embodiments of the present teachings where a wire delivery catheter (220) is guided by a locating device (210). According to some embodiments, the wire delivery catheter (220) has two axial lumens (222, 224), one for a wire (260a) and the other for a locating device (210). The wire delivery catheter (220) enters the right atrium (8) through the lumen (14) of the guide (12). While maintaining the position of the wire delivery catheter (220) inside the right atrium (8), a clinician can extend the locating device (210) distally through the tricuspid valve (2) into the right ventricle (4) in a similar manner with respect to the wire delivery catheter (20) as described herein in accordance with FIGS. 2a and 2b. Similarly, the locating device (210) can have a curved distal portion (212), either preformed or actuated by a clinician, can be extended distally and retracted proximally, or be turned axially as indicated by the double-headed arrows in the FIG. 8a.

Upon entering the right ventricle (4), the distal end (214) of the locating device (210) is positioned at the first location (32) following the methods described herein in accordance with FIGS. 2a-2b, as well as FIG. 7a. Maintaining the position of the locating device (210) steady, the wire delivery catheter (220) is pushed distally toward the tricuspid annulus (3) so that the annulus (3) is sandwiched between the catheter (220) and the locating device (210), as shown in FIG. 8b. A wire (260a) is advanced distally from the wire lumen (224) across the tricuspid annulus (3) and into the right ventricle (4), as shown in FIG. 8b. According to some embodiments, the distal end (214) of the locating device (210) has openings or slots. In some embodiments, when the wire (260a) advances across the tricuspid annulus (3), it enters the openings or slots in the distal end (214) of the locating device (210). In other embodiments, the distal end (214) of the locating device (210) is configured that when a clinician retracts the locating device (210) proximally, he/she would not disturb the wire (260a). According to some embodiments, the design and configuration of the wire (260a) is similar to what is described herein according to FIGS. 4a and 4b. One skilled in the art would understand that the particular embodiments in FIGS. 8a and 8b only illustrate certain aspects of the present teachings and that they should not be viewed as limiting the scope of the present teachings.

According to some embodiments, upon placing the wire (160, 260) across the first location (32) on the tricuspid annulus, the wire delivery catheter (120, 220), the locating catheter (100), and/or the locating device (210) are retracted proximally outside of the body. FIG. 9 illustrates that the wire (160, 260) extends distally from a venous access site, tracks along the lumen of the wire delivery catheter (120, 220), enters into the right atrium (8), crosses the tricuspid annulus (3), and reaches the right ventricle (4). The proximal end of the wire (160, 260) remains outside of the body and is controlled by a clinician. The distal end (162, 262) of the wire (160, 260) remains inside the right ventricle (4). In some embodiments, the wire (160, 260) has a piercing tip which allows it to perforate the tricuspid annulus (3) or has a radio frequency energy delivery tip which delivers a radio frequency energy to the annulus tissue to perforate the tricuspid annulus (3). Additionally, similar to what is described herein according to FIGS. 4a and 4b, the distal portion of the wire is designed to deflect or curl back to prevent inadvertent tissue damage, as shown in FIG. 9.

Figure 10:
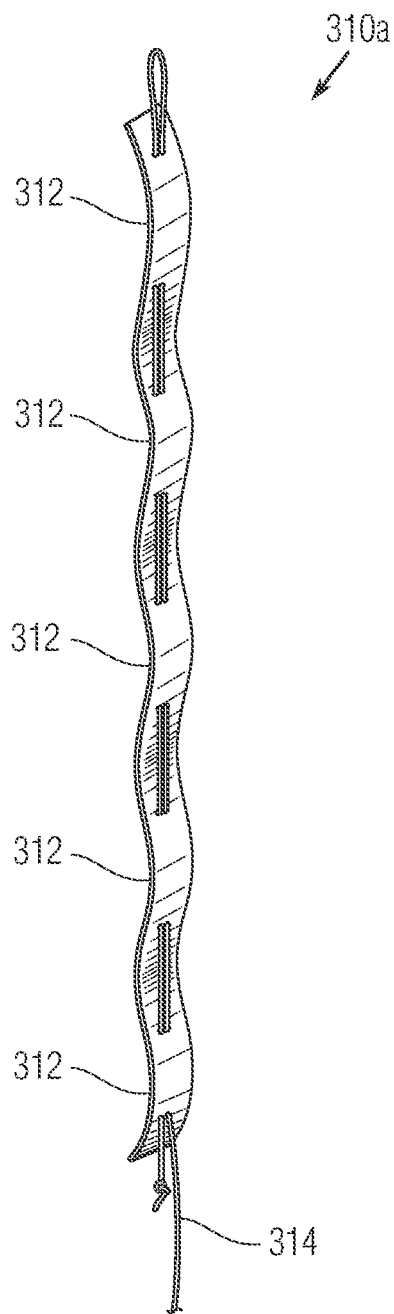
FIG. 10 is a perspective view of an exemplary tissue anchor in accordance with the present teachings.

With the wire (60a, 160a, 260a) in place across the tricuspid annulus (3), in various embodiments, a tissue anchor (310a) is deployed at a location. According to some embodiments, as illustrated in FIGS. 10-12, a first tissue anchor delivery catheter (300) is tracked along the wire (60a, 160a, 260a), across the tricuspid annulus (3), and into the right ventricle (4). In certain embodiments, the tissue anchor delivery catheter (300) is used to deliver a tissue anchor (310a) to the tricuspid annulus (3).

While any tissue anchoring devices known in the art can be used, the particular tissue anchor (310a) in the present teachings, as shown in FIG. 10, is collapsible. In various embodiments, a tissue anchor comprises a plurality of discrete, flat, or flexible anchor elements (312) coupled with a flexible tensile member (314). The anchor elements (312) can be made from a surgical grade fabric material (e.g., a polyester material such as DACRON), in some instances, designed to promote tissue in-growth so that the anchors (310a) become at least in part encased in tissue over-time. The anchor elements (312) are coupled to a tensile member (314), in this example, a suture, by threading the suture distally through the anchor elements (312) and proximally through the anchor elements (312). A slip knot or another type of locking mechanism is formed so that when a proximal end portion of the tensile member (314) is pulled, all of the anchor elements (312) will be drawn together. This leaves a long "tail" of the suture leading from the anchor to the venous access site and the long "tail" can be used for subsequent tensioning and plication, as described herein.

Examples of a tissue anchor (310) and a tissue anchor delivery catheter (300) described in conjunction with the drawings of the present teachings have some similarities to those in U.S. patent application Ser. No. 12/273,670, filed on Nov. 19, 2008, entitled Tissue Anchor and Anchoring System, U.S. patent application Ser. No. 11/174,951, filed on Jul. 5, 2005, entitled Tissue Anchor, Anchoring System and Methods of Using the Same, U.S. patent application Ser. No. 13/777,042, filed on Feb. 26, 2013, entitled Tissue Anchor and Anchoring System, each of which is incorporated by reference herein in its entirety. Though not shown in the exemplary figures, other suitable tissue anchors can also be used. Examples of suitable tissue anchors include, but are not limited to, tissue fasteners, tissue pledgets, or tissue staples etc.

Figure 11A:
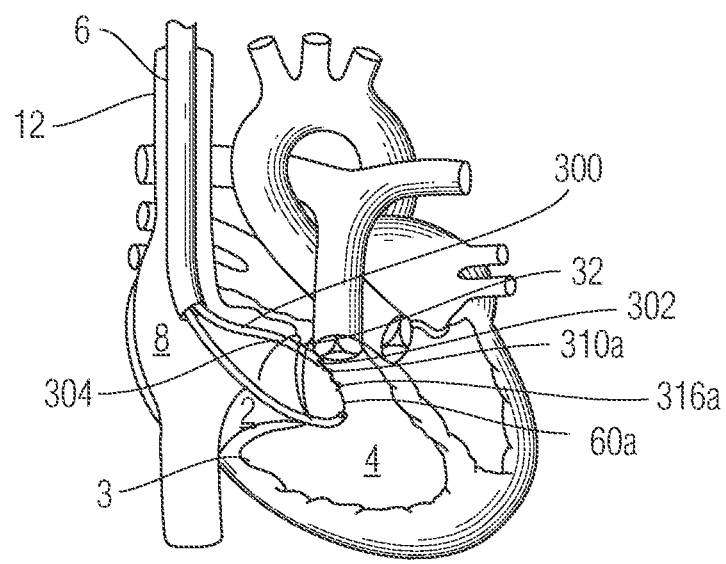
FIGS. 11a-11c are perspective views of an exemplary tissue anchor deployed across the tricuspid annulus in accordance with the present teachings.
Figure 11B:
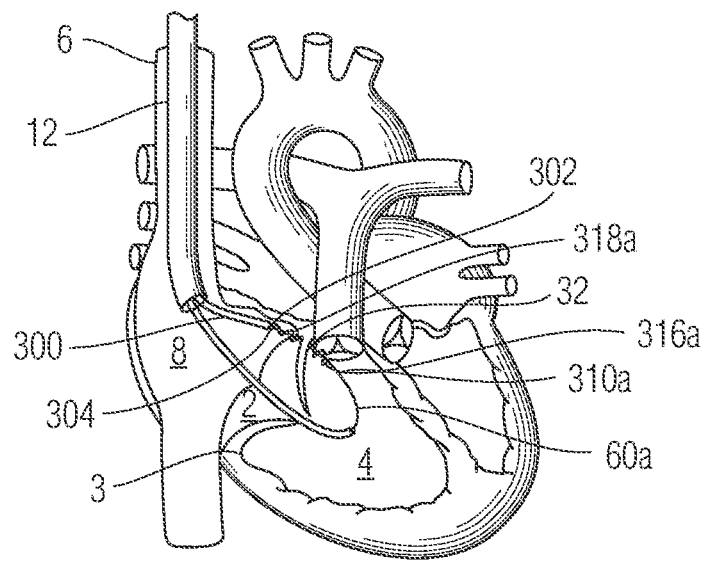
Figure 11C:
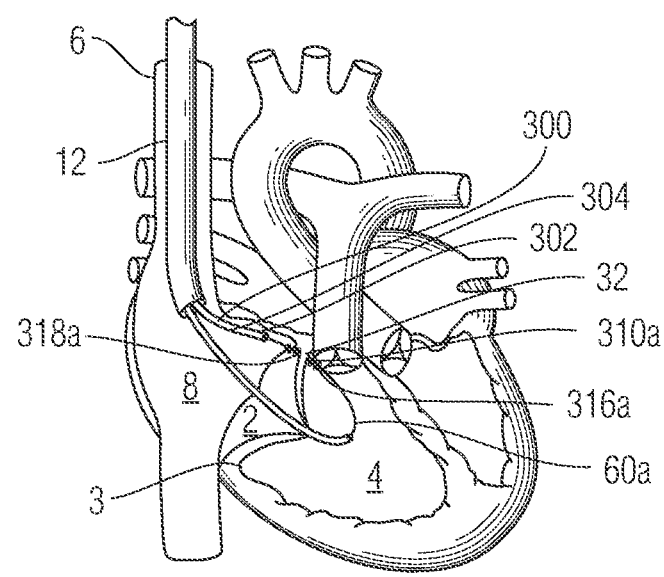
Figure 12A:
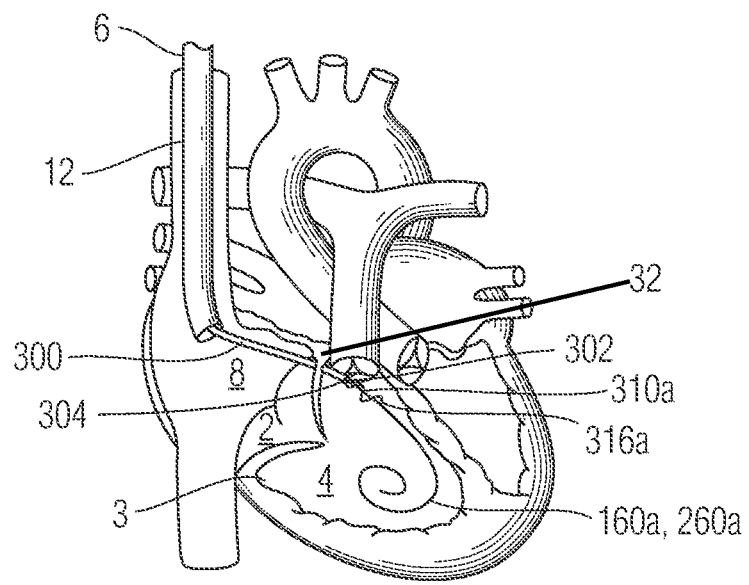
FIGS. 12a-12c are perspective views of an exemplary tissue anchor deployed across the tricuspid annulus in accordance with the present teachings.
Figure 12B:
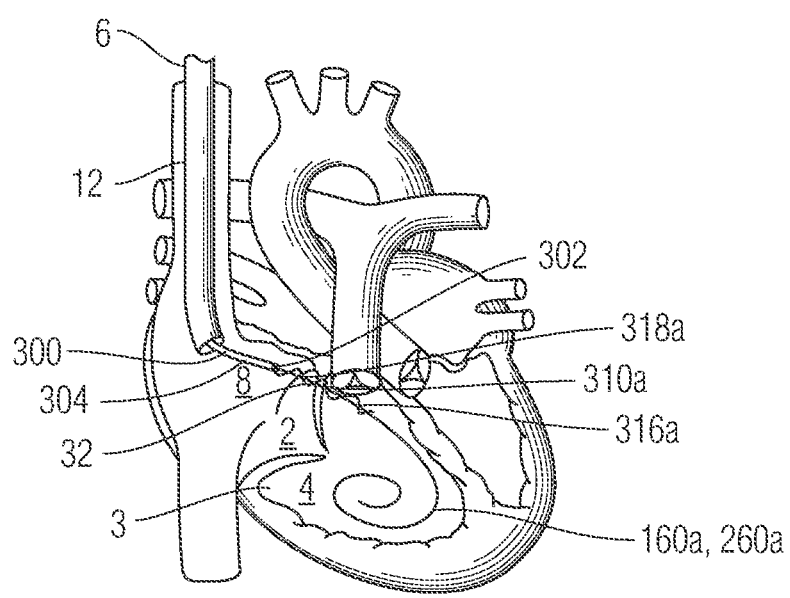
Figure 12C:
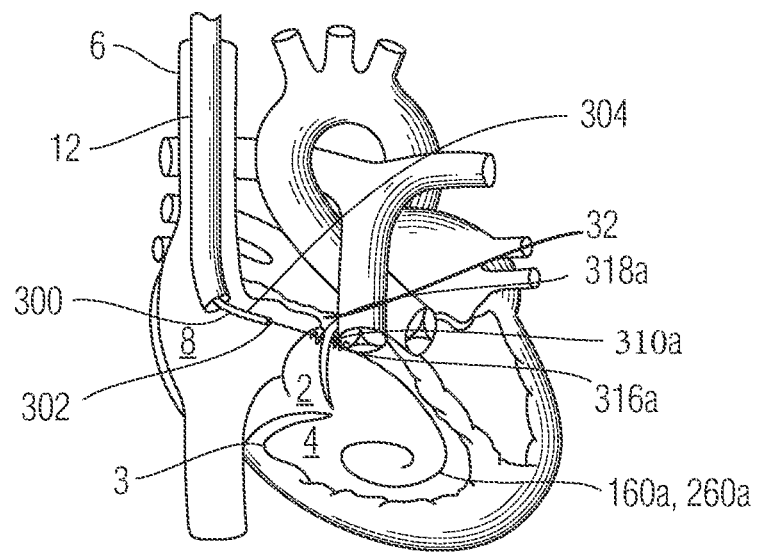

FIGS. 11-12 illustrate an exemplary delivery and deployment of a first tissue anchor (310a) across the tricuspid annulus (3). FIGS. 11a and 12a illustrate the process of exposing of the distal portion (316a) of the tissue anchor (310a) and FIGS. 11b and 12b illustrate the process of exposing the proximal portion (318a) of the tissue anchor (310a), where the tissue anchor tracks along the wire (60a, 160a, 260a) at the location (32) according to the embodiments described in FIGS. 2-9. FIGS. 11c and 12c illustrate an exemplary deployment of the tissue anchor (310a) positioned at the location (32) according to the embodiment described in association with FIGS. 2-9, where the tissue anchor tracks along the wire (60a, 160a, 260a).

Referring to FIGS. 11a and 12a, a tissue anchor delivery catheter (300) holding a tissue anchor (310a) inside its longitudinal lumen (302) tracks along the wire (60a, 160a, 260a), across the tricuspid annulus (3), and into the right ventricle (4). Continuing to referring to FIGS. 11a and 12a, the tissue anchor (310a) is partially pushed distally outside of the distal end (304) of the tissue anchor delivery catheter (300). Once the distal portion (316a) of the tissue anchor (310a) or a sufficient amount of the anchor elements (312, shown in FIG. 10) is exposed inside the right ventricle (4), a clinician stops pushing the tissue anchor (310a) distally and retracts the tissue anchor delivery catheter (300) proximally so that the distal end (304) of the tissue anchor delivery catheter (300) moves proximally across the annulus (3) and back into the right atrium (8). The clinician then exposes the proximal portion (318a) of the tissue anchor (310a) or the remainder of the anchor elements (312) of the tissue anchor (310a) within the right ventricle (4) by further retracting the tissue anchor delivery catheter (300) proximally as shown in FIGS. 11b and 12b.

As illustrated in FIGS. 11c and 12c, to deploy the tissue anchor (310a), the clinician pulls the proximal end of the tensile member (314) such that the anchor elements (312) of the tissue anchor (310a) are drawn together against the opposite sides of the tricuspid annulus (3), thereby securing the first tissue anchor (310a) to the tricuspid annulus (3). As a result, as illustrated in FIGS. 11c and 12c, the first tissue anchor (310a) is deployed across the tricuspid annulus (3) at the first location (32) with the distal portion (316) of the tissue anchor (310a) placed against the atrial side of the tricuspid annulus (3), the proximal portion (318) of the tissue anchor (310a) placed against the ventricle side of the tricuspid annulus (3), and the tensile member (314) of the first tissue anchor (310a) extending proximally through the lumen (302) of the tissue anchor delivery catheter (300) to the outside of the body. According to some embodiments, the wire (60a, 160a, 260a) that marks the first location (32) and maintains the annulus access during the deployment of the first tissue anchor (310a) is then withdrawn proximally outside of the body, while the proximal end of the tensile member (314) is controlled by the clinician from outside of the body.

Although exemplary embodiment herein disclosure proximal and distal portion (316a) of the tissue anchors (310a) are deployed/cinched simultaneously, one skilled in the art should understand that in an alternative embodiment, distal portion (316a) of the tissue anchors (310a) can be deployed/cinched right after being exposed inside the right ventricle (4) and before the tissue anchor delivery catheter (300) being retracted back into the right atrium (8). Upon positioning the deployed/cinched distal portion of the tissue anchor against the right atrium side of the annulus (3), the proximal portion (318a) is then exposed within the right ventricle (4) and further deployed/cinched against the tricuspid annulus (3). One skilled in the art should understand that specific examples disclosed herein should not be viewed as limiting. Similar tissue anchor deployment technique known in the field could also be incorporated herein.

With the first tissue anchor (310a) securely deployed at the first location across the tricuspid annulus (3), the clinician can deploy a second tissue anchor (310b) at a second location (30) according to some embodiments of the present teachings. FIGS. 13-14 illustrate several exemplary deployment of a second tissue anchor (310b) at a second location (30) across the tricuspid annulus (3).

Figure 13A:
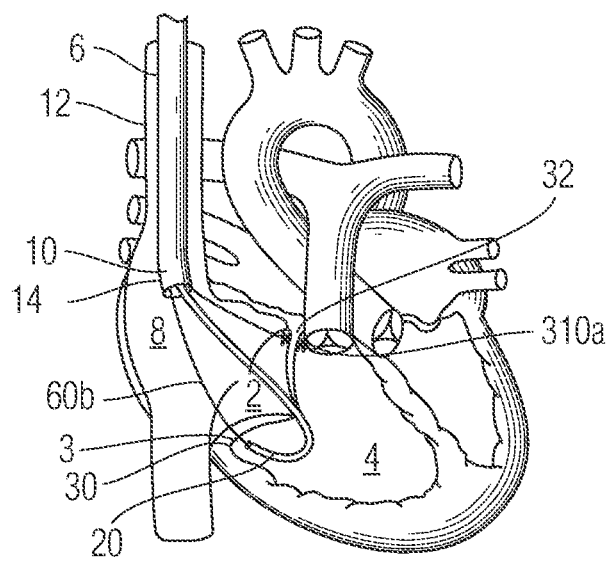
FIGS. 13a-13b are perspective views of an exemplary method where an exemplary second wire extends across the tricuspid annulus in accordance with the present teachings.

According to some embodiments, similar to what is described in FIGS. 2-6, a clinician uses the similar steps to position a wire delivery catheter (20) against the tricuspid annulus (3) from inside the right ventricle (4) at the second location (30). According to some embodiments, the positioning of the wire delivery catheter against the tricuspid annulus includes extending, retracting, turning, or otherwise manipulating the wire delivery catheter (20) to the second location (30) similar to the methods described herein or known to those with ordinary skill in the art. Similar to what is described herein in accordance with the FIGS. 2-6, one end of the second wire (60b) is advanced across the tricuspid annulus (3), captured by the capture basket (44, 52) as illustrated in FIGS. 3a and 3b, and pulled proximally through the lumen (14) of the guide (12) outside of the body. As illustrated in FIG. 13a, it results in that the wire (60) is placed at the second location (30) and both the ends of the wire (60b) are outside of the body.

Figure 13B:
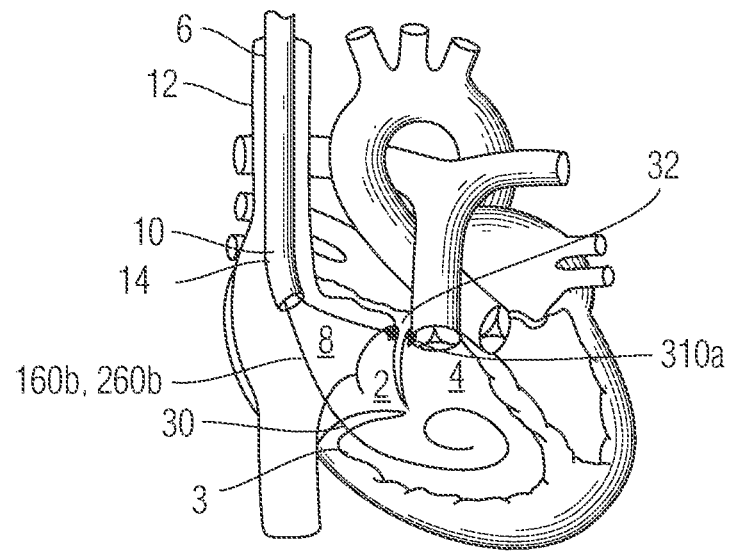

According to alternative embodiments, similar to what is described in FIGS. 7-9, a clinician takes the similar steps to position the wire delivery catheter (120, 220) against the tricuspid annulus (3) from inside the right atrium (8) at a second location (30). According to some embodiments, this is done by extending, retracting, turning, or otherwise manipulating a locating catheter (100) or a locating device (210) at the second location (30) through methods similar to those described herein or known to those with ordinary skill in the art. Similar to what is described in accordance with FIGS. 7-9, the wire delivery catheter (120, 220) is positioned at the second location (30) through magnetic attraction or by the wire delivery catheter design discussed herein. As illustrated in FIG. 13b, a second wire (160b, 260b) is advanced distally across the tricuspid annulus (3) and reaches the right ventricle (4) as described herein. The result is illustrated in FIG. 13b, where one end of the wire (160b, 260b) extends distally through the lumen (14) of the guide (12) and reaches the right ventricle (4). In other words, the distal end of the second wire (160b, 260b) resides inside the right ventricle (4) and the proximal end of the second wire (160b, 260b) resides outside of the body.

Figure 14A:
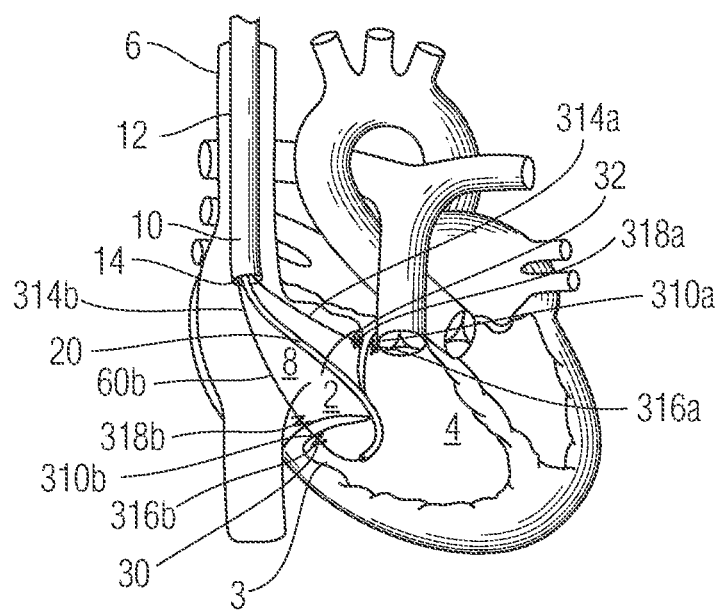
FIGS. 14a-14b are perspective views of an exemplary second tissue anchor deployed across the tricuspid annulus in accordance with the present teachings.
Figure 14B:
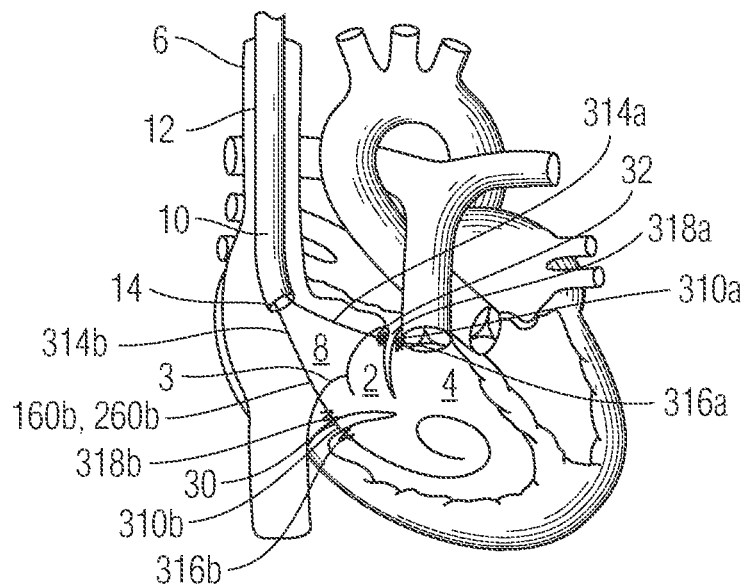

In various embodiments, a second tissue anchor (310b) is deployed at the second location (30) according to various embodiments described herein in accordance with FIGS. 11-12. FIGS. 14a and 14b illustrate the embodiments where the second tissue anchor (310b) is deployed across the tricuspid annulus (3) at the second location (30) with the distal portion (316b) of the second tissue anchor (310b) placed against the ventricle side of the annulus (3), the proximal portion (318b) of the tissue anchor (310b) placed against the atrial side of the annulus (3), and the tensile member (314) of the second tissue anchor (310b) extending proximally through the venous access to the outside of the body. At this point, the second wire (60b, 160b, 260b) can be removed.

Figure 15:
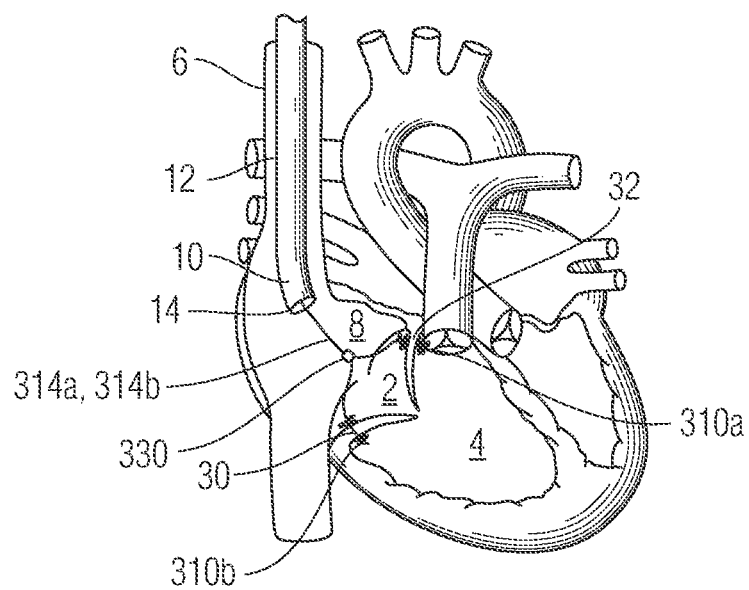
FIG. 15 is a perspective view of applying tension to two exemplary tissue anchors deployed across annulus in accordance with the present teachings.

FIG. 15 illustrates an exemplary bicuspidization of a tricuspid valve (2). According to some embodiments, a clinician applies tension to one or both of the tensile members (314a, 314b) of the tissue anchors (310a, 310b). This tension pulls two tissue anchors (310a) closer to each other, thereby reducing the circumference of the tricuspid annulus (3). This tension, and the reduced distance between the two tissue anchors (310a, b), are maintained by directing a locker member (330) along the tensile members (314a, 314b) towards the tissue anchors (310a, 310b). Suitable lockers include those well known in the art and those described in U.S. application Ser. No. 11/753,921, filed on May 25, 2007, entitled Lockers for Surgical Tensile Members and Methods of Using the Same to Secure Surgical Tensile Members, the disclosure of which is incorporated herein by reference. With the tensile members (314a, 314b) are secured by the locker (330), the excess tensile members (314a, 314b) proximal to the locker (330) can be removed by a cutter, for example, a cutter disclosed in U.S. patent application Ser. No. 11/935,054, filed on Nov. 5, 2007, entitled Suture Cutter and Method of Cutting Suture, the disclosure of which is incorporated herein by reference. The guide (12) along with all the wire delivery catheters (20, 120, 220) and/or the tissue anchor delivery catheter (300) can then be retracted proximally and removed.

FIGS. 16a and 16b illustrate an exemplary process of bicuspidization. According to some embodiments, the first tissue anchor (310a) is deployed at a location at or close to the commissure of the posterior and septal leaflets and the second tissue anchor (310b) is deployed at a location at or close to the commissure of the posterior and anterior leaflets, as illustrated in FIG. 16a. Upon reducing the distance between the two tissue anchors (310a, 310b), the posterior annulus is shortened and the posterior leaflet is effectively eliminated, thereby turning the three-leaflet valve into a two-leaflet valve. In certain instances, the process is called bicuspidization, as illustrated in FIG. 16b.

According to various embodiments of the present teachings, reducing the circumference of the tricuspid annulus (3) facilitates a coaptation of the tricuspid valve (2) leaflets and reduces or eliminates the tricuspid regurgitation jet by at least one degree. According to some embodiments, both the tissue anchors (310a, 310b) are positioned along the posterior annulus. According to other embodiments, at least one tissue anchor (310a) is positioned on the posterior annulus and the other tissue anchor (310b) is placed on the anterior annulus or the septal annulus. According to yet other embodiments, at least one tissue anchor (310a) is placed at a location at or close to the commissure of the posterior and septal leaflets and the other tissue anchor (310b) is placed at a location between the commissure of the posterior and septal leaflets and the commissure of the posterior and anterior leaflets.

According to some embodiments, two tissue anchors (310a and 310b) are deployed around the annulus circumferences. According to other embodiments, more than two tissue anchors (310a, 310b) are deployed. One exemplary embodiment as shown in FIGS. 16c and 16d, includes one tissue anchor (310a) deployed at an location at or close to the commissure of the posterior and septal leaflets, one tissue anchor (310b) deployed at an location at or close to the commissure of the posterior and anterior leaflets, and another tissue anchor (310c) deployed approximately in the middle of the first two. One with ordinary skill in the art would understand that although FIGS. 16a-16d illustrate certain embodiments of the present teachings, other configuration and other locations can also be used for placing the tissue anchor (310a). For example, four or more tissue anchors could be implanted along the posterior annulus of the tricuspid valve. Thus, what is described as to the locations of the tissue anchor (310a) or the number of the tissue anchors (310a) deployed should not be viewed as limiting.

Figure 16E:
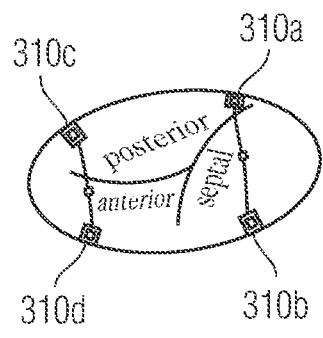
Figure 16F:
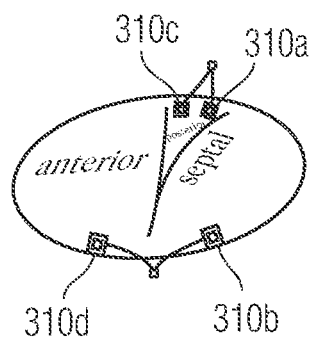

Additionally, although three tissue anchors are illustrated herein, more than three tissue anchors can also be used without departing from the scope of the present teachings. According to some embodiments, tension is applied to all tissue anchors and secured by one locker. According to other embodiments, tension is applied to two of the tissue anchors at a time, for example, as illustrated in FIGS. 16e and 16f.

According to some embodiments, each tissue anchor is deployed sequentially. Specifically, the embodiments described in accordance with FIGS. 2-15 allow a clinician to place a wire (60, 160, 260) at the first location (32), followed by deploying a first tissue anchor (310a) over the wire (60, 160, 260), and then manipulate the same wire delivery mechanism to and place the wire at a second location (30), followed by deploying a second tissue anchor (310b) over the wire (60, 160, 260). According other embodiments, two or more tissue anchors are deployed simultaneously. Specifically, a multi-lumen translation catheter (400) can be used to place two wires at two locations at the same time. According to other embodiments, a catheter with more than two branches can be used to place multiple wires at multiple locations at the same time.

Figure 17:
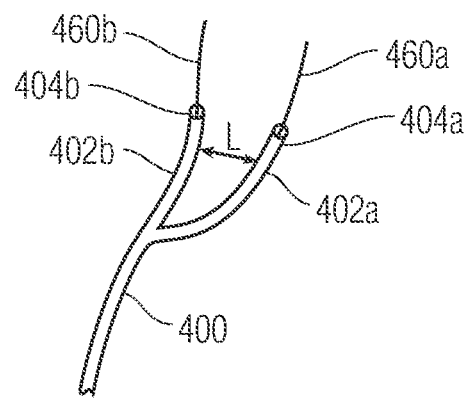
FIG. 17 is a perspective view of an exemplary multi-lumen translation catheter in accordance with the present teachings.

FIGS. 17-19 illustrate the use of a multi-lumen translation catheter (400) to place two wires (460a, 460b) across the tricuspid annulus (3). According to one embodiment, as illustrated in FIG. 17, a multi-lumen translation catheter (400) comprises a first catheter member (402a) having a first lumen (404a) for a first wire (460a) and a second catheter member (402b) having a second lumen (404b) for a second wire (460b). The first and second wires (460a, 460b) are slidably disposed within the first and second catheter lumens (404a, 404b), respectively. There is a pre-defined lateral distance "L" between the first catheter member (402a) and the second catheter member (402b).

Figure 18A:
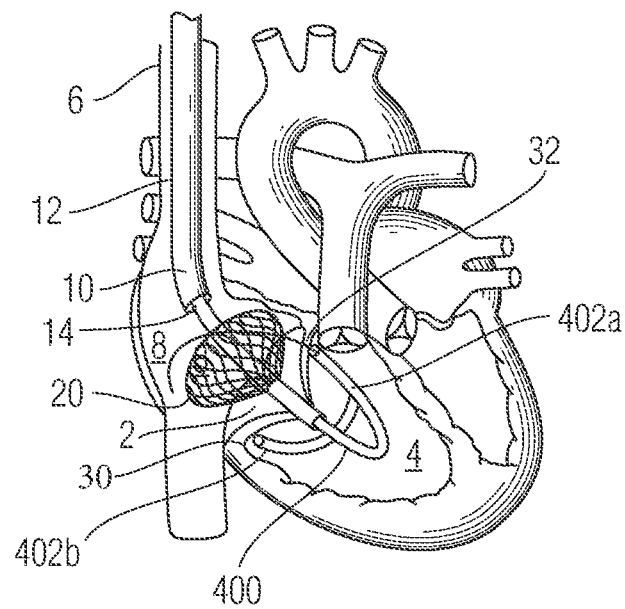
FIGS. 18a-18b are perspective views of an example of placing two exemplary wires across the tricuspid annulus with an exemplary multi-lumen translation catheter in accordance with the present teachings.

According to some embodiments, a multi-lumen translation catheter (400) is delivered to the right ventricle (4) and positioned against the tricuspid annulus (3) through a wire delivery catheter (20), as illustrated in FIG. 2a. According to some embodiments, similar to what is described herein in accordance with FIGS. 2-6, upon the wire delivery catheter (20) being positioned against the tricuspid annulus (3) from inside the right ventricle (4), the first wire (460a), extending through the lumen (404a) of the first catheter member (402a), is placed across the tricuspid annulus (3). The wire delivery catheter (20) is retracted proximally, exposing the second catheter member (402b) of the multi-lumen translation catheter (400), as illustrated in FIG. 18a. Once outside of the distal end (24) of the wire delivery catheter (20), the second catheter member (402b) expands laterally away from the first catheter member (402a) to a pre-defined distance. Without losing the placement of the first wire (460a), a clinician can turn the multi-lumen translation catheter (400) and/or the wire delivery catheter (20) so that the second catheter member (402b) is positioned at a second location (30). A second wire (460b) is then advanced across the tricuspid annulus (3) following the steps described herein and shown in FIGS. 4a and 4b.

According to some embodiments, both the wires (460a, 460b) is captured by the capture device and the distal ends of the both wires (460a, 460b) are then withdrawn through the lumen (14) of the guide (12) outside of the body. As a result, as illustrated in FIG. 18b, two wires are placed at two locations, which can be used to facilitate the deployment of two tissue anchors (310a), following the steps discussed above and in accordance with FIGS. 11a-11c.

Figure 19A:
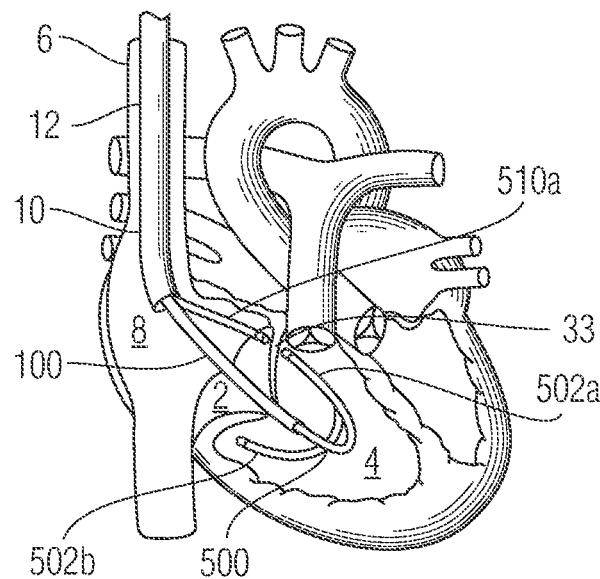
FIGS. 19a-19b are perspective views of an example of placing two exemplary wires across the tricuspid annulus with an exemplary multi-lumen translation catheter in accordance with the present teachings.

According to other embodiments as illustrated in FIG. 19a, a multi-lumen translation catheter or device (500) is delivered though the lumen of a locating catheter (100) to the right ventricle (4). As the distal end (104) of the locating catheter (100) is positioned against the annulus (3), a first catheter member (502a) is placed at a first location (32), attracting a first wire delivery catheter (510a) and facilitating the placement of a first wire (560a). The locating catheter (100) is retracted proximally, exposing a second catheter member (502b) of the multi-lumen translation catheter (500) as illustrated in FIG. 19a. Once outside of the distal end (104) of the locating catheter (100), the second catheter member (502b) expands laterally away from the first catheter member (502a) to a pre-defined distance. Without losing the placement of the first wire delivery catheter (510a), a clinician can turn the multi-lumen translation catheter (500) and/or the locating catheter (100) so that the second catheter member (502b) is positioned at a second location (30). The second catheter member (502b) attracts the second wire delivery catheter (510b) and facilitates the placement of the second wire (560b) across the tricuspid annulus (3) as shown in FIG. 19b.

According to some embodiments, the multi-lumen translation catheter is placed at two locations first and two wires are placed across the tricuspid annulus simultaneously or sequentially. Alternatively, in other embodiments, a first catheter member of a multi-lumen translation catheter is positioned at a first location first and a first wire is placed across the tricuspid annulus; a second catheter member of the multi-lumen translation catheter is positioned at a second location and a second wire is placed across the tricuspid annulus.

Figure 18B:
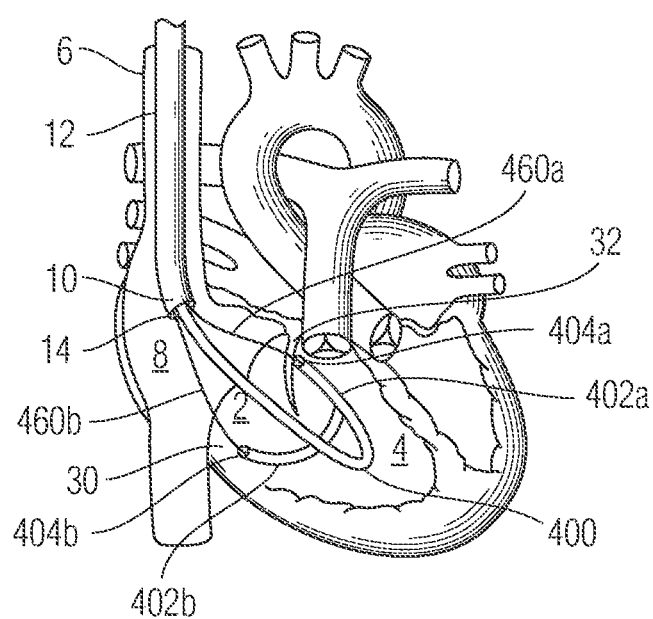
Figure 19B:
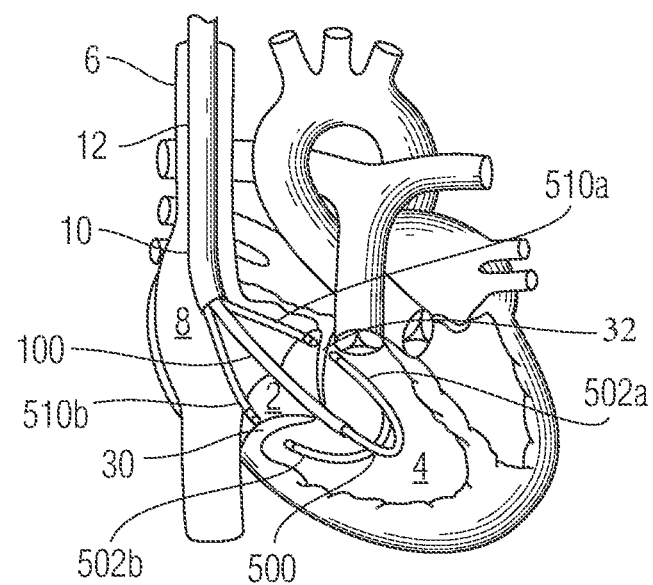

As a result, as illustrated in FIGS. 18b and 19b, two wires are placed at two locations, followed by the deployment of two tissue anchors according to the steps or steps similar with those discussed herein and in accordance with FIGS. 11-16.

Although an exemplary multi-lumen translation catheter is described above, one with ordinary skill in the art would understand that a three or more branched catheter can be used without departing from the spirit of the present teachings. The multi-lumen translation described in conjunction with the drawings of the present teachings have some similarities to those in U.S. patent application Ser. No. 11/685,239, filed on Mar. 13, 2007, entitled Systems and Methods for Introducing Elements Into Tissue; U.S. patent application Ser. No. 11/685,240, filed on Mar. 13, 2007, entitled Tissue Anchors, Systems, and Methods, and Devices; U.S. patent application Ser. No. 11/685,242, filed on Mar. 13, 2007, entitled Devices and Methods For Introducing Elements into Tissue; and U.S. patent application Ser. No. 13/282,139, filed on Oct. 26, 2011, entitled Hand Operated Device for Controlled Deployment of a Tissue Anchor and Method of Using the Same; each of which is incorporated in its entirety by reference herein.

Above described embodiment discloses the use of one locker member maintaining tension on two or more tensile members. In alternative embodiments of the present teaching, tricuspid annulus can be plicated by a chain of tissue anchors. In some embodiments, two or more tissue anchors are connected together by a tensile member. Plication happens by pulling said tensile member and thereby drawing all tissue anchors together.

Figure 20A:
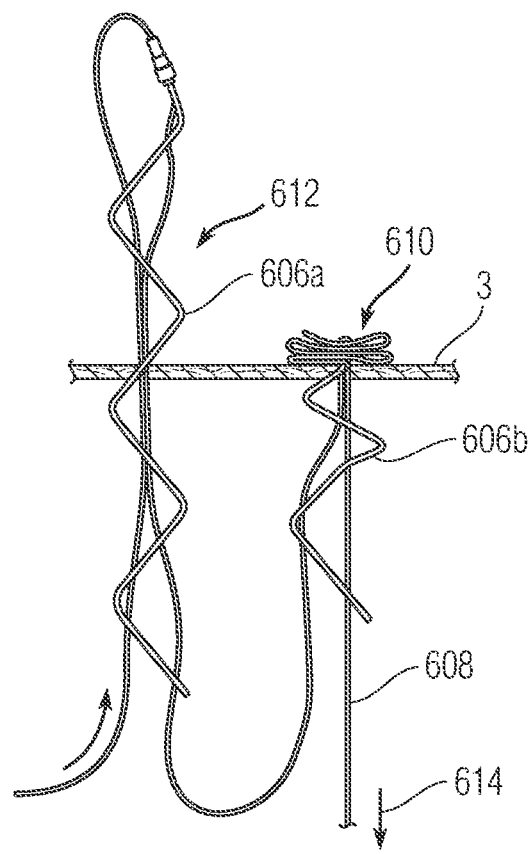
FIGS. 20a-20c are perspective views of placing multiple tissue anchors across the tricuspid annulus in accordance with the present teachings.
Figure 20B:
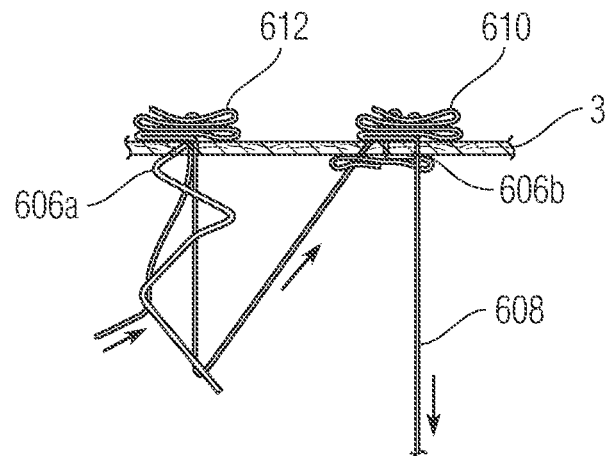
Figure 20C:
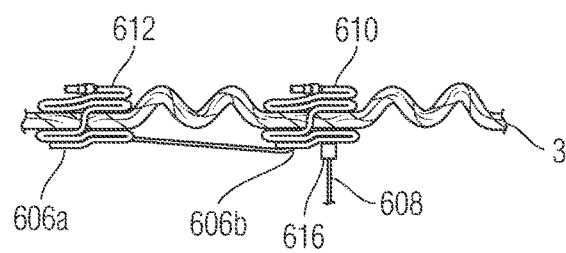

FIGS. 20A-C illustrates one embodiment of the present teaching where a single tensile member may be used to deploy, fasten and draw together at least two separate tissue anchors. As shown in FIG. 20A, first and second tissue anchors (610, 612) are deployed at spaced apart locations along the tricuspid valve annulus (3). Each tissue anchors (610, 612) includes an elongate strip (606a, 606b) of flexible material, such as fabric or other material as described above, as well as a single tensile member (608) extending through each of the elongate strips (606a, 606b). Upon deployment of the two tissue anchors (610, 612), the free end (614) of the tensile member (608) is pulled thereby securely fastening the first tissue anchor (610) as shown in FIG. 20A and subsequently securely fastening the second tissue anchor (612) to the annulus (3) tissue as shown in FIG. 20B. Upon further tensioning of the tensile member (608), the tissue anchors (610, 612) will be drawn together to plicate the tissue therebetween as shown in FIG. 20C. A locker member (616) may then be used to lock in the desired amount of plication by lock the free end (614) of the tensile member (608) as shown in FIG. 20C. The free end (614) of the tensile member (608) may then be cut to appropriate length. One skilled in the art should understand that more than two tissue anchors could be used with this teaching.

Figure 21A:
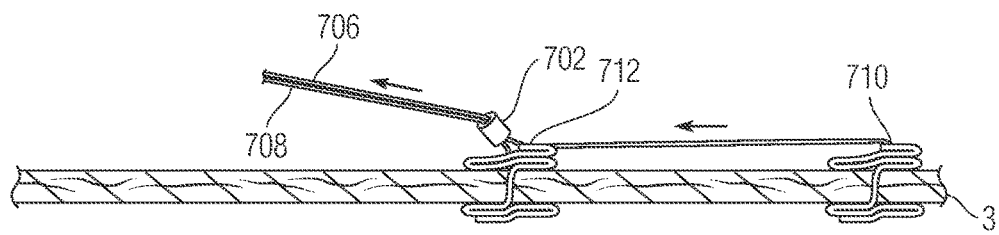
FIGS. 21a-21c are perspective views of placing multiple tissue anchors across the tricuspid annulus in accordance with the present teachings.
Figure 21B:
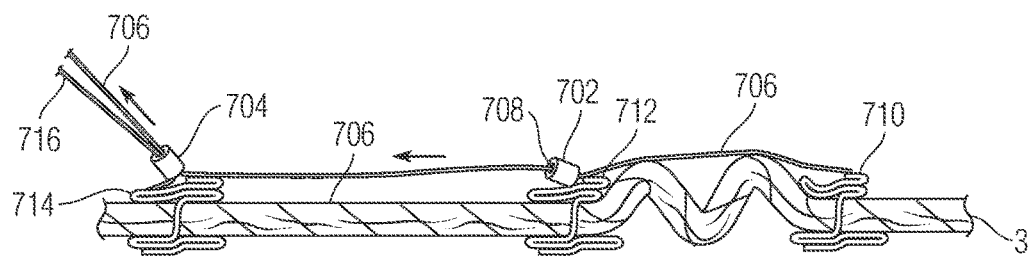
Figure 21C:
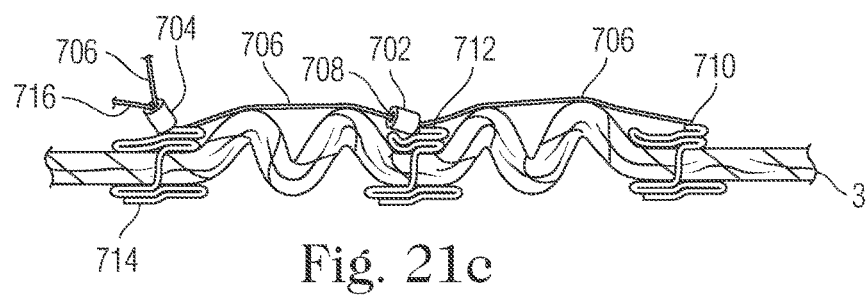

FIGS. 21A-21C illustrates another embodiment of the present teaching where tricuspid annulus is plicated by a chain of tissue anchors. Similar to above described methods, two tissue anchors (710,712) are secured to tricuspid annulus (3), each with a tensile member (706, 708) extending proximally. FIG. 21A illustrates that the tensile members (706, 708) extend through a first locker member (702). Suitable locker members can include those described in U.S. patent application Ser. No. 11/425,731 and U.S. patent application Ser. No. 11/753,921, the disclosures of which are incorporated herein by reference, or other suitable lockers known within the art. The first locker member (702) can include a locker body having a passageway through which the tensile members (706, 708) extend. A slidable member can be positioned within the passageway, which can be moved from a latent condition to an activated condition to prevent the tensile members (706, 708) from moving relative to the locker body. Both tensile members (706, 708) are pulled proximally by the clinician. Upon plicating annulus tissue between the first tissue anchor (710) and the second tissue anchor 712, the tensile members (706, 708) are locked by the first locker member (702) to preserve the plications created by tensioning as illustrated in FIG. 21B. According to some embodiments of the present teaching, a suture cutter is then advanced along tensile members (706, 708) to just proximal to the first locker member (702). In one embodiment, tensile member (708) from the second tissue anchor (712) is cut while the tensile member (706) from the first tissue anchor (710) remains intact. In another embodiment, tensile member (706) from the second tissue anchor (710) is cut while the tensile member (708) from the first tissue anchor (712) remains intact.

According to some embodiments, to create a chain of plications, a clinician can then repeat method of tissue plication described above and extend the first tensile member (706) from the first tissue anchor (710) to a second locker member (704). As illustrated in FIG. 21B, a third tissue anchor (714) is further deployed across the posterior annulus (3) with a third tensile member (716) extending proximally. Upon plicating annulus tissue between the first tissue anchor (710), and the third tissue anchor (714), the tensile members (706, 716) are locked by the second locker member (704) to preserve the plication created by tensioning as illustrated in FIG. 21C. The second locker member (704) can be the same as the first locker member (702), or if desired, a different suitable locker can be used. When tension is applied to the tensile members (706, 716), the tissue of the posterior annulus (3) is further plicated. This plication further reduces the size of the tricuspid valve orifice.

According to some embodiment, a suture cutter can then be advanced to cut the tensile members (706, 716) just proximal to the second locker member (704). However, if plication is not complete such that the posterior, anterior and septal leaflets do not coapt, then additional tissue anchors can be advanced to the annular tissue. Accordingly, at least one of the tensile members (706, 716) remains intact to be tensioned with a subsequently positioned tissue anchor.

According to various embodiments of the present teachings, a radioopaque marker or textured surface can be used to make the device visible by using radiographic imaging equipment such as an X-ray, magnetic resonance, ultrasound or other imaging technique. A marker disclosed herein may be applied to any part of the guide, catheter, or devices disclosed in present teachings. A radioopaque marker can be sewed, adhered, swaged riveted, or otherwise placed and secured on the guide, catheter, and/or devices, The radioopaque marker may be made from a material selected from tantalum, tungsten, platinum, iridium, gold, an alloy thereof, or another material known to those with ordinary skill in the art. The radioopaque marker can also be made from cobalt, fluorine, or another paramagnetic material, or another MR visible material known to those with ordinary skill in the arts. Additionally, a contrast media injected into the atrium, ventricle, or artery may also be used to confirm the positioning under a fluoroscope.

Unless otherwise defined, all technical and scientific terms used herein have the same meaning as commonly understood by one of ordinary skill in the art to which this present teachings belong. Methods and materials similar or equivalent to those described herein can be used in the practice or testing of the present teachings. In case of conflict, the specification, including definitions, controls. In addition, the materials, methods, and examples are illustrative only and not intended to be limiting.

What is claimed is:

1. A method for percutaneously anchoring tissue within a heart of a patient comprising the steps of:
locating a first tissue location inside a right ventricle;
advancing a wire from the right ventricle through the tricuspid annulus to the right atrium at the first location;
capturing the wire within the right atrium and pulling the wire outside of a body of the patient, whereby the wire extends within the right ventricle and the right atrium;
deploying a distal portion of a first tissue anchor at the first tissue location such that the distal portion is deployed into the right ventricle;
deploying a proximal portion of the first tissue anchor at the first tissue location such that the proximal portion is deployed inside the right atrium;
locating a second tissue location inside the right ventricle;
deploying a distal portion of a second tissue anchor at the second tissue location such that the second anchor tissue is deployed into the right ventricle;

deploying a proximal portion of the second tissue anchor at the second tissue location such that the proximal portion is deployed inside the right atrium; and plicating the tissue by changing the distance between the first and second tissue anchors.

2. The method of claim 1, wherein at least one of the first and the second locations is on a tricuspid annulus of the heart.

3. The method of claim 1, further comprising the step of advancing a tissue anchor catheter along the wire to the first location.

4. The method of claim 1, wherein the step of locating the second location occurs after the deployment of the first tissue anchor.

5. The method of claim 1, wherein the step of locating the second location occurs prior to the deployment of the first tissue anchor.

6. A method for repairing a tricuspid valve of a patient's heart comprising the steps of:

positioning a wire delivery catheter through the tricuspid valve into a right ventricle with a distal end of the wire delivery catheter contacting a tricuspid annulus at a first location which is inside the right ventricle;

advancing a wire through an axial lumen of the wire delivery catheter such that a first end of the wire passes from the right ventricle across the tricuspid annulus to a right atrium at the first location;

capturing the first end of the wire with a capture device that is deployed inside the right atrium;

retracting the capture device proximally away from the heart such that the first end of the wire extends outside of a body of the patient; and deploying a first tissue anchor at the first location using the wire as a guide, the first tissue anchor being deployed such that a distal portion of the first tissue anchor is positioned against the tricuspid annulus within the right ventricle, and a proximal portion of the first tissue anchor is positioned against the tricuspid annulus within the right atrium.

7. The method of claim 6, further including the steps of:

tracking a first tissue anchor delivery catheter over the wire, crossing the tricuspid annulus with a distal end of the first tissue anchor delivery catheter being disposed inside the right ventricle;

deploying the first tissue anchor by passing the first tissue anchor though a lumen of the first tissue anchor delivery catheter; and retracting the end of the wire back into the axial lumen of the wire delivery catheter.

8. The method of claim 6, further including the steps of:

positioning the wire delivery catheter through the tricuspid valve into the right ventricle with the distal end of the wire delivery catheter contacting the tricuspid annulus at a second location which is inside the right ventricle, the second location being spaced from the first location;

advancing a wire through an axial lumen of the wire delivery catheter such that the first end of the wire passes from the right ventricle across the tricuspid annulus to the right atrium at the second location;

capturing the first end of the wire with the capture device that is deployed inside the right atrium;

retracting the capture device proximally away from the heart such that the first end of the wire extends outside of a body of the patient;

deploying a second tissue anchor at the second location using the wire as a guide, the second tissue anchor being deployed such that a distal portion of the second tissue anchor is positioned against the tricuspid annulus within the right ventricle, and a proximal portion of the second tissue anchor is positioned against the tricuspid annulus within the right atrium; and placating the tricuspid valve by reducing the distance between the first and second tissue anchors.

9. The method of claim 6, wherein the capture device comprises a capture basket that moves between a radially deployed position and a retracted position, the basket being configured to receive and capture the first end of the wire.

10. The method of claim 9, wherein the basket comprises a wire mesh formed of a memory shape material.

11. The method of claim 6, wherein the tissue anchor comprises:

a generally flexible anchor member capable of being inserted through tissue and moving between an elongate configuration and a shortened configuration suitable for anchoring against at least one side of the tissue, said anchor member having a proximal end portion, a distal end portion, and a compressible intermediate portion between said proximal end portion and said distal end portion, and a tensioning member extending through the proximal end portion to the distal end portion and back to an anchor point at the proximal end portion, the tensioning member being operatively connected to said anchor member such that said anchor member can slide relative to said tensioning member, said tensioning member capable of being pulled to cause said anchor member to move relative to said tensioning member from said elongate configuration to said shortened configuration wherein the compressible intermediate portion can compress and thereby adjust to the thickness of the tissue between the proximal and distal end portions.

12. A method for repairing a tricuspid valve of a patient's heart comprising:

positioning a wire delivery catheter through a tricuspid valve into a right ventricle;

slidably disposing a multi-lumen translation catheter within a lumen of the wire delivery catheter;

slidably disposing a first wire within a first catheter member of the multi-lumen translation catheter;

slidably disposing a second wire within a second catheter member of the multi-lumen translation catheter;

positioning a distal end of the first catheter member at a first location;

advancing a first end of the first wire from the right ventricle across the tricuspid annulus to a right atrium at the first location;

expanding the second catheter member of the multi-lumen translation catheter and positioning a distal end of the second catheter member against the tricuspid annulus at a second location;

advancing a first end of the second wire from the right ventricle across the tricuspid annulus to the right atrium at the second location;

capturing the first ends of the first and second wires with a capture device;

retracting the capture device proximally away from the heart and thereby extending the first ends of the first and second wires outside of the body;

tracking a first tissue anchor delivery catheter over the first wire, a second tissue anchor delivery catheter over the second wire, crossing the tricuspid annulus with distal ends of the first and second tissue anchor delivery catheters inside the right ventricle;

deploying the first and second tissue anchors such that distal portions of the first and second tissue anchors are positioned against the tricuspid annulus from inside the right ventricle, and proximal portions of the first and second tissue anchors are positioned against the tricuspid annulus from inside the right atrium; and plicating tissue of the tricuspid annulus by reducing the distance between the first and second tissue anchors.

13. The method of claim 12, wherein each of the first and second tissue anchor comprises:

a generally flexible anchor member capable of being inserted through tissue and moving between an elongate configuration and a shortened configuration suitable for anchoring against at least one side of the tissue, said anchor member having a proximal end portion, a distal end portion, and a compressible intermediate portion between said proximal end portion and said distal end portion, and a tensioning member extending through the proximal end portion to the distal end portion and back to an anchor point at the proximal end portion, the tensioning member being operatively connected to said anchor member such that said anchor member can slide relative to said tensioning member, said tensioning member capable of being pulled to cause said anchor member to move relative to said tensioning member from said elongate configuration to said shortened configuration wherein the compressible intermediate portion can compress and thereby adjust to the thickness of the tissue between the proximal and distal end portions.

* * * * *